(12) United States Patent
Silverman et al.

(10) Patent No.: US 6,184,234 B1
(45) Date of Patent: Feb. 6, 2001

(54) INSECTICIDAL N-(SUBSTITUTED ARYLMETHYL)-4-[BIS(SUBSTITUTED PHENYL OR PYRIDYL)METHYL] PIPERIDINES

(75) Inventors: Ian R. Silverman, Moorestown; Daniel H. Cohen, Princeton; John W. Lyga, Basking Ridge, all of NJ (US); Steven W. Szczepanski, Walnut Creek, CA (US); Syed F. Ali, Yardville, NJ (US); Thomas G. Cullen, Milltown, NJ (US); Robert N. Henrie, II, Pennington, NJ (US); Clinton J. Peake, Trenton, NJ (US)

(73) Assignee: FMC Corporation, Philadelphia, PA (US)

( * ) Notice: Under 35 U.S.C. 154(b), the term of this patent shall be extended for 0 days.

(21) Appl. No.: 09/414,375

(22) Filed: Oct. 7, 1999

Related U.S. Application Data

(63) Continuation-in-part of application No. 08/981,456, filed as application No. PCT/US96/07206 on May 17, 1996, now Pat. No. 6,030,987, which is a continuation of application No. 08/444,698, filed on May 19, 1995, now abandoned, which is a division of application No. 08/389,675, filed on Feb. 16, 1995, now Pat. No. 5,639,763, which is a continuation-in-part of application No. 08/204,033, filed on Mar. 1, 1994, now abandoned.

(51) Int. Cl.$^7$ .......................... A01N 43/40; A01N 43/54; C07D 405/10

(52) U.S. Cl. .......................... 514/321; 514/256; 514/318; 514/326; 544/333; 546/193; 546/197; 546/207; 546/208; 546/209; 546/210; 546/211

(58) Field of Search .......................... 544/333; 546/193, 546/197, 207, 208, 209, 210, 211; 514/256, 318, 321, 326

(56) References Cited

U.S. PATENT DOCUMENTS 3,920,442 * 11/1975 Albert et al. .................... 504/243
4,632,925 * 12/1986 Mullin et al. .................... 514/326

FOREIGN PATENT DOCUMENTS

94/18172 * 8/1994 (WO).

* cited by examiner

Primary Examiner—Ceila Chang
(74) Attorney, Agent, or Firm—FMC Corporation

(57) ABSTRACT

Compounds of the following structure, the corresponding N-oxides and agriculturally acceptable salts thereof, are disclosed as effective insecticides:

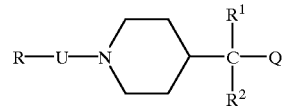

wherein
U is —(CH$_2$)$_n$—;
Q is hydroxy; and
R is:

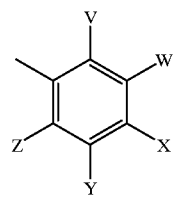

and wherein
V, W, Y, and Z are each hydrogen;
X is a five- or six-membered heterocycle; optionally substituted with bromine, chlorine, fluorine, cyano, alkyl, haloalkyl, alkoxy, haloalkoxy, alkoxyalkyl, haloalkoxyalkyl, or aminocarbonyl; and the heterocycle is optionally connected to the phenyl ring through a —O—, —S—, —(CH$_2$)$_p$, —C(O)—, or —O—(CR$^3$R$^4$)$_q$ linkage;
R$^1$ and R$^2$ are independently selected from phenyl or pyridyl substituted with pentahalothio, haloalkylthio, haloalkylsulfinyl, or haloalkylsulfonyl; phenyl substituted with —OC(M)$_2$O—, where M is bromine, chorine or fluorine, to provide a dihalobenzodioxolyl fused ring; or pyridyl substituted with —OC(M)$_2$O— to provide a dihalodioxolenopyridyl fused ring;
R$^3$ and R$^4$ are independently selected from hydrogen and methyl;
n and p are independently 1, 2, or 3; and
q is 1 or 2; with the proviso that at least one of R$^1$ and R$^2$ is substituted in the para position of the phenyl ring or the 5-position of the 2-pyridyl ring; each alkyl portion of said optional substituent on X wherein the optional substituent is alkyl, haloalkyl, alkoxyl, haloalkoxyl, alkoxyalkyl, or haloalkoxyalkyl contains from 1 to 4 carbon atoms; each heterocycle contains from 1 to 4 nitrogen atoms, 1 or 2 oxygen or sulfur atoms, or 1 or 2 nitrogen atoms and an oxygen or sulfur atom; and the corresponding N-oxides and agriculturally acceptable salts.

17 Claims, No Drawings

INSECTICIDAL N-(SUBSTITUTED ARYLMETHYL)-4-[BIS(SUBSTITUTED PHENYL OR PYRIDYL)METHYL] PIPERIDINES

This is a continuation-in-part U.S. patent application of Ser. No. 08/981,456, filed Aug. 11, 1998, now U.S. Pat. No. 6,030,987, which is a national phase entry of PCT/US96/07206 filed May 17, 1996; which is a continuation of U.S. Ser. No. 08/444,698, filed May 19, 1995, now abandoned; which is a divisional application of Ser. No. 08/389,675, filed Feb. 16, 1995, now U.S. Pat. No. 5,639,763; which is a continuation-in-part application of Ser. No. 08/204,033, filed Mar. 1, 1994, now abandoned.

The present invention relates to methods for controlling insects. In particular, it relates to control by the application of certain novel N-(substituted arylmethyl)-4-[bis (substituted phenyl or pyridyl)methyl]piperidines to the locus where insect control is needed.

It has now been found that compounds of the following structure and their corresponding N-oxides, as well as their agriculturally acceptable salts, are active as insecticides:

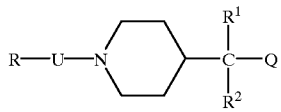

in which U is —$(CH_2)_n$; Q is hydroxy; R is:

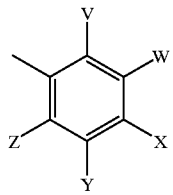

in which V, W, Y, and Z are each hydrogen; X is a five- or six-membered heterocycle; optionally substituted with halogen, cyano, alkyl, haloalkyl, alkoxyl, haloalkoxyl, alkoxyalkyl, haloalkoxyalkyl, or aminocarbonyl; and the heterocycle is optionally connected to the phenyl ring through a —O—, —S—, —$(CH_2)_p$—, —C(O)—, or —$O(CR^3R^4)_q$— linkage; $R^1$ and $R^2$ are independently selected from phenyl or pyridyl substituted with haloalkyl, haloalkoxy, pentahalothio, haloalkylthio, haloalkylsulfinyl, or haloalkylsulfonyl; phenyl substituted with —OC(M)$_2$O—, where M is halogen, to provide a dihalobenzodioxolyl fused ring; or pyridyl substituted with —OC(M)$_2$O— to provide a dihalodioxolenopyridyl fused ring; $R^3$ and $R^4$ are independently selected from hydrogen and methyl; n and p are independently 1, 2, or 3; and q is 1 or 2; with the proviso that at least one of $R^1$ and $R^2$ is substituted in the para position of the phenyl ring or the 5-position of a 2-pyridyl ring; each alkyl portion of said optional substituent on X wherein the optional substituent is alkyl, haloalkyl, alkoxyl, haloalkoxyl, alkoxyalkyl, or haloalkoxyalkyl contains from 1 to 4 carbon atoms; halogen means bromine, chlorine, or fluorine; each heterocycle contains from 1 to 4 nitrogen atoms, or 1 or 2 oxygen or sulfur atoms, or 1 or 2 nitrogen atoms and an oxygen or sulfur atom; and the corresponding N-oxides and agriculturally acceptable salts thereof.

An embodiment of the present invention is that when q is 2, —$O(CR^3R^4)_q$ is —$O(CHCH_3CHCH_3)$—, —$O(C(CH_3)_2CH_2)$— or —$O(CH_2C(CH_3)_2)$—.

Preferred are those compounds in which in X the heterocycle is selected from 1,2,4-oxadiazolyl, oxazolinyl, pyridazinyl, pyrazinyl, pyrazolyl, pyridyl, pyrimidinyl, pyrolyl, tetrazolyl, 1,2,3-thiadiazolyl, 1,3,5-triazinyl, and 1,2,4-triazolyl, optionally substituted with halogen, cyano, alkyl, haloalkyl, alkoxy, haloalkoxy, alkoxyalkyl, or haloalkoxyalkyl, and the optional linkage is selected from —O—, —$(CH_2)_p$—, or —$O(CHR^3)_q$—; $R^1$ and $R^2$ are independently selected from trifluoromethylphenyl, trifluoromethoxyphenyl, trifluoromethylpyridyl, trifluoromethoxypyridyl, pentafluorothiophenyl, trifluoromethylthiophenyl, trifluoromethylsulfinylphenyl, trifluoromethylsulfonylphenyl, 2,2-dihalo-1,3-benzodioxolyl, pentafluorothiopyridyl, trifluoromethylthiopyridyl, trifluoromethylsulfinylpyridyl, trifluoromethylsulfonylpyridyl, and 2,2-dihalo-1,3-dioxoleno[4,5-b]pyridyl; n is 1, and p and q are independently 1 or 2; with the proviso that halogen means chlorine or fluorine; and the corresponding N-oxides and agriculturally acceptable salts.

Particularly preferred are those compounds in which X is a heterocycle selected from 1,2,4-oxadiazol-5-yl, oxazolin-2-yl, pyrazol-3-yl, pyridin-2-yl, pyrimidin-2-yl, pyrol-3-yl, 2H-tetrazol-5-yl, 1,2,3-thiadiazol-4-yl, 1,2,4-triazol-3-yl, optionally substituted with halogen, cyano, alkyl, haloalkyl, or alkoxyalkyl, and the optional linkage is selected from —O—, —$OCH_2$—, or —$OCH(CH_3)$; $R^1$ and $R^2$ are independently selected from p-trifluoromethoxyphenyl, p-trifluoromethylphenyl, 5-trifluoromethylpyrid-2-yl, 5-trifluoromethoxypyrid-2-yl, p-pentafluorothiophenyl and 2,2difluoro1,3-benzodioxol-5-yl; and the corresponding N-oxides and agriculturally acceptable salts. More preferred are those compounds in which X is 2H-tetrazol-5-yl optionally substituted in the 2 position; X is pyridin-2-yl optionally substituted in the 6-position; and X is pyrimidin-2-yl, optionally substituted in the 4-position.

The N-oxides include the piperidine N-oxides, the pyridine N-oxides, or both.

Preferred moieties substituting the five- or six- membered heterocycle representing X is —$CH_2OCH_3$ and the haloalkyl —$(CH_2)_rF$, where r is 1, 2, or 3, $CHF_2$, and $CF_3$.

The compounds of the present invention were prepared by methods generally known to those skilled in the art. In the method shown in Schema 1, where $R^1$ and $R^2$ are the same, ethyl piperidin4-ylcarboxylate was reacted with either an appropriately substituted alkyl halide, for example, 4-methoxyphenylmethyl bromide, or with an appropriately substituted aldehyde under reductive conditions, for example, 4-phenoxybenzaldehyde, affording the corresponding ethyl N-substituted alkylpiperidin-4-ylcarboxylate (A). Intermediate (A) was then treated with more than two molar equivalents of the Grignard reagent of an appropriately substituted halide, for example, 4-trifluoromethoxyphenyl magnesium bromide, yielding the desired N-(substituted alkyl)4-[bis(substituted) hydroxymethyl]piperidine (I), for example, N-(4-methoxyphenylmethyl)-4[bis(4-trifluoromethoxyphenyl) hydroxymethyl]piperidine (Compound 1). Example 1 provides a detailed description of how these reactions are conducted.

Compound (I) of the present invention, as depicted in Schema 1, can be further reacted to obtain additional compounds within the scope of Compound (I). For example, compounds where $R^1$ and $R^2$ are phenyl substituted with haloalkylthio can be converted to the corresponding compounds where $R^1$ and $R^2$ are phenyl substituted with haloalkylsulfinyl or haloalkylsulfonyl by the mild oxidation of the haloalkylthio moiety with sodium perborate [Synth. Commun.; 1993, 23 (6), 765–769].

Another method, again for cases where $R^1$ and $R^2$ are the same, is shown in Schema 2. In this method ethyl piperidin-4-ylcarboxylate is reacted with diethyl carbamoyl chloride, under basic conditions, affording the corresponding intermediate, ethyl N-diethylaminocarbonylpiperidin-4-yl-carboxylate (B). Intermediate (B) is treated with more than two molar equivalents of the Grignard reagent of an appropriately substituted halide, yielding the corresponding N-diethylaminocarbonyl-4-[bis(substituted phenyl or pyridyl)hydroxymethyl]piperdine (C). Intermediate (C) is then treated with lithium aluminum hydride, affording the 4-[bis(substituted phenyl or pyridyl)hydroxymethyl] piperidine (II), for example, 4-[bis (4trifluoromethoxyphenyl)hydroxymethyl]piperidine. As depicted in Schema 2a, intermediate (II) may be reacted with either an appropriately substituted alkyl halide or with an appropriately substituted aldehyde, as previously described, affording the desired N-(substituted alkyl)-4-[bis(substituted phenyl or pyridyl)hydroxymethyl]piperidine (I), for example, N-[4-(2-methyltetrazol-5-yl)phenylmethyl]-4-[bis (4-trifluoromethoxyphenyl)hydroxymethyl]piperidine (Compound 9).

For the preparation of those compounds in which $R^1$ and $R^2$ may be pyridyl, the appropriate pyridyl bromide is lithiated at −78° C. with tert-butyllithium, and the resulting product is used as described for the magnesium Grignard reagents.

The preparation of intermediate (II) using the method described above provided relatively low yields of (II). In a preferred method to prepare the intermediate 4-[bis (substituted phenyl)hydroxymethyl]piperidine (II), ethyl piperidin-4-ylcarboxylate was reacted with chlorotrimethyl-silane under basic conditions in diethyl ether, affording ethyl N-(trimethylsilyl)piperidin-4-yl-carboxylate. The so-prepared ethyl carboxylate was then reacted with more than two molar equivalents of the Grignard reagent of an appropriately substituted halide, a method previously described, affording intermediate (II) Both steps of this method provided product in good yield. Example 3 provides a detailed description of how this reaction is conducted. Schema 3 shows this method.

The intermediate 4-[bis(substituted phenyl or pyridyl) hydroxymethyl]piperidine (II) described above, can also be reacted, as shown in Schema 2a, with an appropriately substituted acid chloride, for example, 4-(1-methyltetrazol-5-yl)benzoyl chloride, under basic conditions, yielding the corresponding N-(substituted carbonyl)-4-[bis-(substituted phenyl or pyridyl)hydroxymethyl]piperidine (G). Intermediate (G) is reduced with borane-methyl sulfide complex, affording the desired N-(substituted alkyl)-4-[bis (substituted)hydroxymethyl]piperidine (I), for example, N-[4-(1-methyltetrazol-5-yl)phenylmethyl]-4-[bis(4-trifluoromethoxyphenyl)hydroxymethyl]piperidine (Compound 8).

Schema 4 shows the method used when $R^1$ and $R^2$ are not the same. Here 4-aminocarbonylpiperidine is reacted with an appropriately substituted alkyl halide, for example, 4-(1, 3-dioxolan-2-yl)phenylmethyl chloride, under basic conditions, affording the corresponding N-(substituted alkyl)-4-aminocarbonylpiperidine (H). Treatment of intermediate (H) with phosphorous oxychloride yields the corresponding N-(substituted alkyl)-4-cyanopiperidine (J), which is in turn reacted with the Grignard reagent of an appropriately substituted halide, for example, 2-trifluoromethoxyphenylmagnesium bromide, yielding the corresponding N-(substituted alkyl)-4-(substituted carbonyl)piperidine (K). Intermediate (K) is reacted with a different Grignard reagent of an appropriately substituted halide, for example, 4-trifluoromethoxyphenylmagnesium bromide, yielding the desired N-(substituted alkyl)-4-[di (substituted phenyl)hydroxymethyl]piperidine (I), for example, N-[4-(1,3-dioxolan-2-yl)phenylmethyl]-4-[(4-trifluoromethoxyphenyl)( 2-trifluoromethoxyphenyl) hydroxymethyl]piperidine (Compound 103).

In an alternate one-step route, the dehydroxylated compounds (IB) are also prepared by the reduction of N-(substituted alkyl))-4-[bis(substituted phenyl or pyridyl) hydroxymethyl]piperidines (I) with trifluoroacetic acid and triethylsilane in methylene chloride.

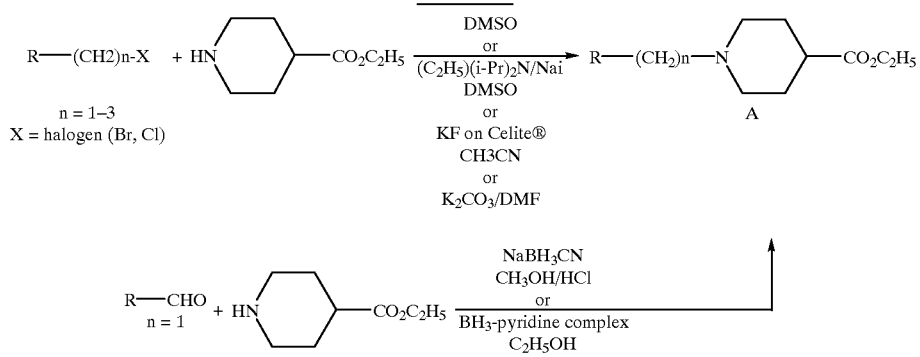

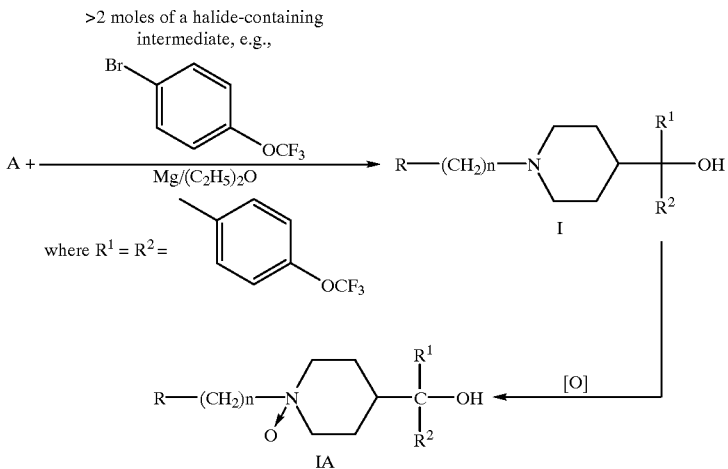
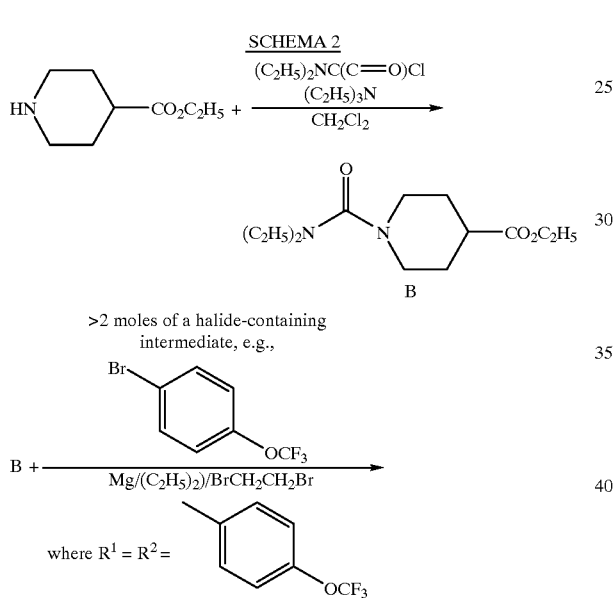
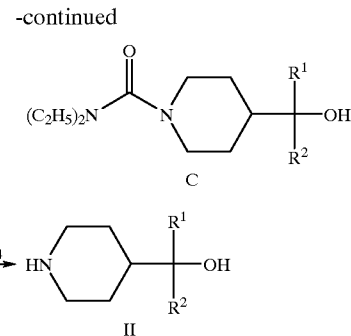
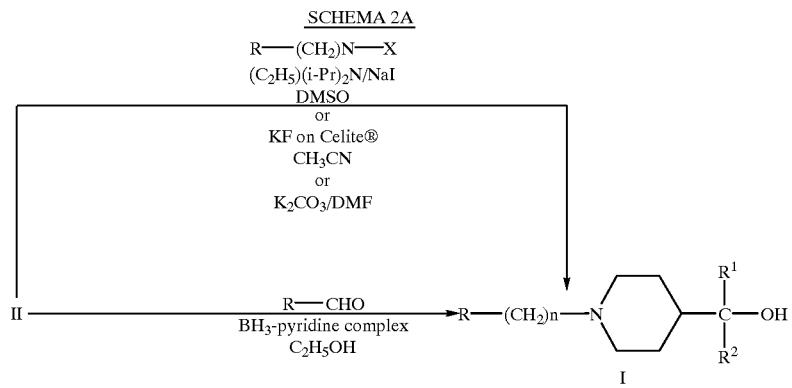

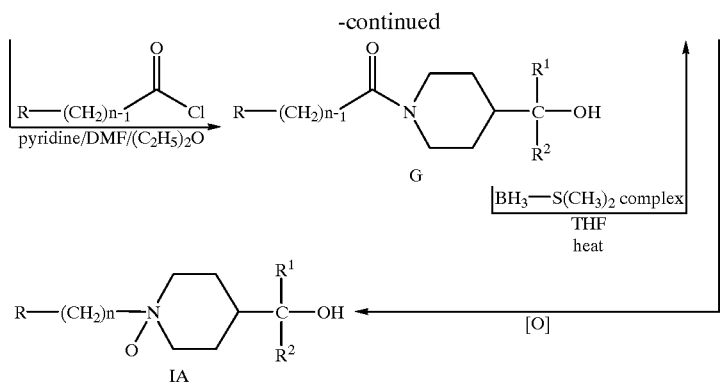

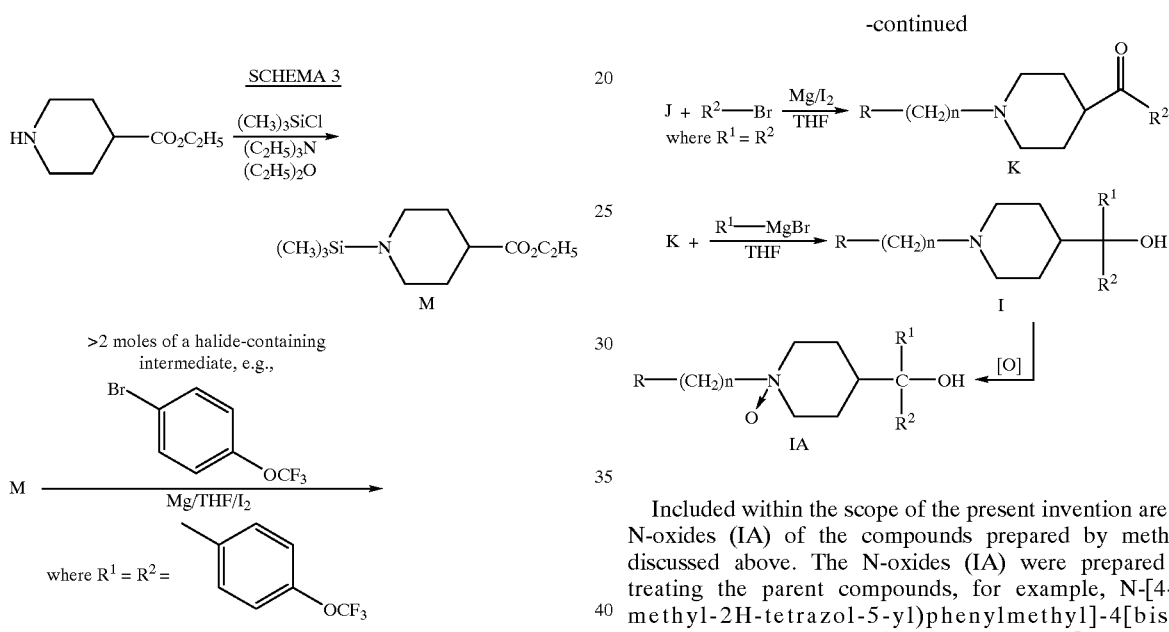

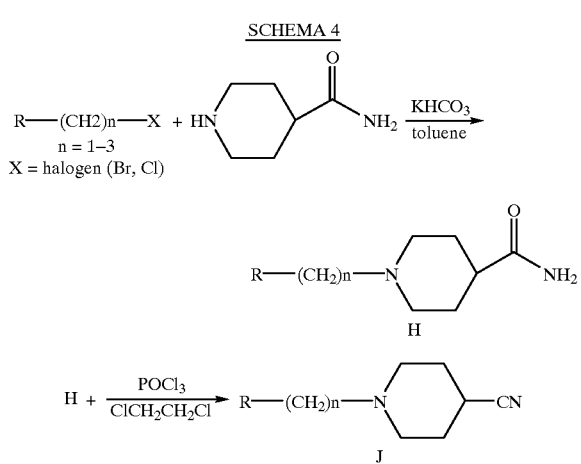

Included within the scope of the present invention are the N-oxides (IA) of the compounds prepared by methods discussed above. The N-oxides (IA) were prepared by treating the parent compounds, for example, N-[4-(2-methyl-2H-tetrazol-5-yl)phenylmethyl]-4[bis(4-trifluoromethylphenyl)hydroxymethyl]piperidine (Compound 31) with an oxidizing agent, such as 3-chloroperoxybenzoic acid, yielding the corresponding N-oxide, for example, N-[4-(2-methyl-2H-tetrazol-5-yl) phenylmethyl]-4-[bis(4-trifluoromethylphenyl) hydroxymethyl]piperidine N-oxide (Compound 32). Example 10 provides a detailed description of how this reaction is conducted.

The following examples illustrate general methods by which the compounds of the present invention were prepared.

EXAMPLE 1

Synthesis of N-(4-Methoxyphenylmethyl)-4-[bis(4-trifluoromethoxyphenyl)hydroxymethyl]piperidine (Compound 1)

To a stirred mixture of 1.1 grams (0.045 gram-atom) of magnesium turnings in 30 mL of diethyl ether was added dropwise 15 mL of a solution of 11.0 grams (0.045 mole) of 4-trifluoromethoxyphenyl bromide in 30 mL of diethyl ether. Once the reaction had started, the remaining 15 mL of the bromide solution was added portionwise during a 45 minute period. When the reaction subsided, a solution of 5.0 grams (0.018 mole) of ethyl N-(4-methoxyphenylmethyl) piperidin-4-ylcarboxylate in 20 mL of diethyl ether was added dropwise during a five minute period. Upon completion of the addition, the reaction mixture was heated to reflux, where it stirred for about 30 minutes. The reaction mixture was then allowed to cool to ambient temperature, where it stirred for about 18 hours. After this time an aqueous solution saturated with ammonium chloride was added dropwise to quench the reaction. The mixture was then partitioned between water and diethyl ether. The diethyl ether layer was separated and washed first with a solution saturated with sodium chloride and then with water. The organic layer was dried with magnesium sulfate and filtered. The filtrate was concentrated under reduced pressure to a residual oil. The oil was subjected to column chromatography on silica gel, with 10% diethyl ether in hexane, 100% diethyl ether, and 10% methanol in diethyl ether as eluants. The product-containing fractions were combined and concentrated under reduced pressure, yielding 6.7 grams of N-(4-methoxyphenylmethyl)-4-[bis(4-trifluoromethoxyphenyl)hydroxymethyl]piperidine, mp 86–96° C. The NMR spectrum was consistent with the proposed structure.

EXAMPLE 2

Synthesis of N-[2-(4-methoxyphenyl)ethyl]-4-[bis (4-trifluoromethoxyphenyl)hydroxymethyl)] piperidine (Compound 2)

Step A Synthesis of ethyl N-[2-(4-methoxyphenyl)ethyl] piperidin-4-ylcarboxylate as an intermediate A stirred mixture of 5.0 grams (0.032 mole) of ethyl piperidin-4-ylcarboxylate, 5.4 grams (0.032 mole) of 1-(2-chloroethyl)-4-methoxybenzene and 4.4 grams (0.032 mole) of potassium carbonate in 50 mL of dried N,N-dimethylformamide was heated at 70° C. for about 16 hours. After this time the reaction mixture was cooled and partitioned between diethyl ether and water. The organic layer was separated and washed with water and then with an aqueous solution saturated with sodium chloride. The organic layer was dried with magnesium sulfate and filtered. The filtrate was concentrated under reduced pressure to a residue, which was subjected to column chromatography on silica gel, with diethyl ether/hexane mixtures as eluants. The product-containing fractions were combined and concentrated under reduced pressure, yielding 2.4 grams of ethyl N-[2-(4-methoxyphenyl)ethyl]piperidin-4-ylcarboxylate. The NMR spectrum was consistent with the proposed structure.

Step B Synthesis of N-[2-(4-methoxyphenyl)ethyl]-4-[bis (4-trifluoromethoxyphenyl)hydroxymethyl]piperidine (Compound 2)

This compound was prepared in a manner analogous to that of Example 1, with 1.6 grams (0.005 mole) of ethyl N-[2-(4-methoxyphenyl)ethyl]piperidin- 4-ylcarboxylate, 2.4 grams (0.010 mole) of 4-trifluoromethoxyphenyl bromide, and 0.3 gram (0.011 gram-atom) of magnesium turnings in about 35 mL of diethyl ether as reagents. This reaction differed from Example 1 in that once the Grignard reaction commenced, the ethyl N-[2-(4-methoxyphenyl) ethyl]piperidin-4-ylcarboxylate was added to the diethyl ether solution of 4-trifluoromethoxyphenyl bromide. The combination was then added dropwise to the reaction mixture, thereby introducing the piperidin-4-ylcarboxylate to the reaction mixture as the Grignard reagent was forming. Upon completion of addition, the reaction mixture was stirred at ambient temperature for about 18 hours. After this time an aqueous solution saturated with ammonium chloride was added dropwise to quench the reaction. The reaction mixture was then extracted with methylene chloride. The combined extracts were washed with a dilute aqueous solution of hydrochloric acid and then with an aqueous solution saturated with sodium chloride. The organic layer was dried with magnesium sulfate and filtered. The filtrate was concentrated under reduced pressure to a residue, which was subjected to column chromatography on silica gel, with hexane/diethyl ether and ethyl acetate/methanol combinations as eluants. A second column chromatography on silica gel was required, with diethyl ether as the eluant, to afford pure product. The product-containing fractions were combined and concentrated under reduced pressure, yielding 0.3 gram of N-[2-(4-methoxyphenyl)ethyl]-4-[bis(4-trifluoromethoxyphenyl)hydroxymethyl]piperidine. The NMR spectrum was consistent with the proposed structure.

EXAMPLE 3

An Alternate Synthesis of 4-[bis(4-trifluoromethoxyphenyl)hydroxymethyl]piperidine for Use as an Intermediate Step A Synthesis of ethyl N-(trimethylsilyl)piperidin-4-ylcarboxylate as an intermediate Under a nitrogen atmosphere, a stirred solution of 100.0 grams (0.64 mole) of ethyl piperidin-4-ylcarboxylate and 94 mL (0.67 mole) of triethylamine in 1400 mL of diethyl ether was cooled to 15° C., and a solution of 86 mL (0.68 mole) of chlorotrimethylsilane in 100 mL of diethyl ether was added dropwise during a 30 minute period. Upon completion of the addition, the thick reaction mixture was stirred vigorously for one hour while warming to ambient temperature. The reaction mixture was then filtered, and the collected solid was washed with diethyl ether. The combined wash and filtrate were concentrated under reduced pressure to a residual oil. The oil was distilled under reduced pressure, yielding 115.0 grams (79% yield) of ethyl N-(trimethylsilyl)piperidin-4-ylcarboxylate, bp 75° C./0.1 mm Hg. The NMR spectrum was consistent with the proposed structure.

Step B Synthesis of 4-[bis(trifluoromethoxyphenyl) hydroxymethyl]piperidine as an intermediate A stirred mixture of 5.0 grams (0.021 mole) of 4-trifluoromethoxyphenyl bromide, 13.8 grams (0.570 gram-atom) of magnesium turnings, and a crystal of iodine in 25 mL of anhydrous tetrahydrofuran was warmed to 50–60° C. Once the Grignard reaction commenced, 500 mL of anhydrous tetrahydrofuran was added, and the reaction mixture temperature was adjusted to 45° C. To this was added a solution of 53.0 grams (0.230 mole) of ethyl N-(trimethylsilyl)piperidin-4-ylcarboxylate and 128.8 grams (0.534 mole) of 4-trifluoromethoxyphenyl bromide in 475 mL of anhydrous tetrahydrofuran at a rate to maintain the reaction mixture temperature at 45–55° C. Upon completion of the addition, the reaction mixture heated at reflux for about two hours, after which the reaction mixture was poured into a stirred mixture of 550 mL of an aqueous solution saturated with ammonium chloride and 200 grams of ice. The mixture was then extracted with 650 mL of ethyl acetate. The organic layer was shaken with one 250 mL portion of an aqueous solution saturated with sodium bicarbonate, one 250 mL portion of aqueous 10% sodium hydroxide solution, and with two 200 mL portions of an aqueous solution saturated with sodium chloride. The organic layer was dried with sodium sulfate and filtered. The filtrate was concentrated under reduced pressure, yielding 110 grams of residual oil. The oil was triturated with 500 mL of petroleum ether, and 67.0 grams of solid 4-[bis (trifluoromethoxyphenyl)hydroxymethyl]piperidine was collected by filtration. The filtrate was cooled, and an additional 15.5 grams of solid 4-[bis (trifluoromethoxyphenyl)hydroxymethyl]piperidine was collected by filtration. The total yield was 82%. The NMR spectrum was consistent with the proposed structure.

EXAMPLE 4

Synthesis of N-[4-(methylcarbonylamino) phenylmethyl]-4-[bis(4-trifluoromethoxyphenyl) hydroxymethyl]piperidine (Compound 3)

Step A Synthesis of N-phenylmethyl-4-[bis(4-trifluoromethoxyphenyl)hydroxymethyl]piperidine as an intermediate This compound was prepared in a manner analogous to that of Step B of Example 2, with 6.0 grams (0.024 mole) of ethyl N-phenylmethylpiperidin-4-ylcarboxylate, 1.8 grams (0.073 gram-atom) of magnesium turnings, and 17.5 grams (0.073 mole) of 4-trifluoromethoxyphenyl bromide in about 80 mL of tetrahydrofuran as reagents. The yield of N-phenylmethyl-4-[bis(4-trifluoromethoxyphenyl) hydroxymethyl]piperidine was 9.7 grams. The NMR spectrum was consistent with the proposed structure.

Step B Synthesis of N-phenylmethyl-4-[bis(4-trifluoromethoxyphenyl)hydroxymethyl]piperidine hydrochloride as an intermediate A stirred solution of 1.0 gram (0.002 mole) of N-phenylmethyl-4-[bis(4-trifluoromethoxyphenyl) hydroxymethyl]piperidine in 30 mL of diethyl ether was cooled to 0° C., and hydrogen chloride gas was bubbled in. An oily solid precipitate formed. Upon completion of precipitation, the reaction mixture was taken up in 25 mL of hexane and stored in a refrigerator for about 18 hours. After this time the supernatant liquid was decanted from the precipitate. The precipitate was then stirred with about 20 mL of diethyl ether, and the mixture was concentrated under reduced pressure to a residue. The solid residue was stirred with about 20 mL of hexane, which was then decanted from the solid. The solid was dried under reduced pressure, yielding 0.8 gram of N-phenylmethyl-4-[bis(4-trifluoromethoxyphenyl)hydroxymethyl]piperidine hydrochloride. The NMR spectrum was consistent with the proposed structure.

Step C Synthesis of 4-[bis(4-trifluoromethoxyphenyl) hydroxymethyl]piperidine as an intermediate Under a nitrogen atmosphere, 0.8 gram of 10% palladium on charcoal (catalyst) was placed in the reaction vessel. To this were cautiously added 25 mL of nitrogen-purged methanol, a solution of 0.8 gram (0.001 mole) of N-phenylmethyl-4-[bis(4-trifluoromethoxyphenyl) hydroxymethyl]piperidine hydrochloride in 10 mL of methanol, and then 0.9 gram (0.010 mole) of ammonium formate. Upon completion of addition, the reaction mixture was heated at reflux for about 45 minutes. The reaction mixture was then cooled to ambient temperature and diluted with 1:1-methylene chloride/methanol. The mixture was filtered through a pad of diatomaceous earth/fiberglass, and the filtrate was concentrated at about 30° C. under reduced pressure to a residue. The residue was taken up in about 70 mL of ice/water and made basic with aqueous 5% sodium hydroxide solution. The mixture was extracted with methylene chloride, and the extract was washed with an aqueous solution saturated with sodium chloride. The organic layer was then dried with sodium sulfate. The mixture was filtered, and the filtrate was concentrated under reduced pressure to a residue. The residue was stirred with petroleum ether, and 0.5 gram of solid 4-[bis(4-trifluoromethoxyphenyl)hydroxymethyl]piperidine was collected by filtration. The NMR spectrum was consistent with the proposed structure.

Step D Synthesis of N-[4-(methylcarbonylamino) phenylmethyl]-4-[bis-(4-trifluoromethoxyphenyl) hydroxymethyl]piperidine (Compound 3)

To a stirred solution of 0.4 gram (0.0008 mole) of 4-[bis(4-trifluoromethoxyphenyl)hydroxymethyl]piperidine in 10 mL of dimethyl sulfoxide was added a mixture of 0.2 gram (0.0008 mole) of 4-(methylcarbonylamino) phenylmethyl chloride and 0.6 mL (0.003 mole) of N,N-diisopropylethylamine. Upon completion of addition, the reaction mixture was stirred at ambient temperature for about 18 hours. After this time the reaction mixture was partitioned between an aqueous solution saturated with sodium bicarbonate and ethyl acetate. The organic layer was separated and washed with an aqueous solution saturated with sodium chloride. The organic layer was then concentrated under reduced pressure to a residue, which was subjected to column chromatography on silica gel, with methylene chloride and mixtures of 10–50% acetone in methylene chloride as eluants. The product-containing fractions were combined and concentrated under reduced pressure, yielding about 0.3 gram of N-[4-(methylcarbonylamino)phenylmethyl]-4-[bis(4-trifluoromethoxyphenyl)hydroxymethyl]piperidine. The NMR spectrum was consistent with the proposed structure.

EXAMPLE 5

Synthesis of N-(4-Propoxyphenylmethyl)-4-[bis(4-trifluoromethylphenyl)hydroxymethyl]piperidine (Compound 102)

Step A Synthesis of 4-propoxyphenylmethyl chloride as an intermediate

A mixture of 53.8 grams (0.33 mole) of 4-propoxybenzaldehyde, 200 mL of ethanol, and 200 mL of tetrahydrofuran was stirred, and 3.3 grams (0.09 mole) of sodium borohydride was added portionwise during a 30 minute period. The reaction caused the reaction mixture temperature to rise to about 45° C. Upon completion of the addition, the reaction mixture was stirred for one hour and then poured into 500 mL of water containing 50 grams of ammonium chloride. The mixture was extracted with two 500 mL portions of diethyl ether, and the combined extracts were washed with one 500 mL portion of an aqueous solution saturated with sodium chloride. The organic layer was dried with magnesium sulfate and filtered. The filtrate was concentrated under reduced pressure, yielding 53.6 grams of white solid. The solid was dissolved in 75 mL of methylene chloride and 0.75 mL of pyridine was added. The solution was added dropwise to a cold (10° C.), stirred solution of 28 mL (0.38 mole) of thionyl chloride in 350 mL of methylene chloride. The complete addition required one hour, during which time the reaction mixture was maintained at 10° C. Upon completion of the addition, the reaction mixture was stirred for one hour and poured into a solution of 350 mL of water containing 100 mL of an aqueous solution saturated with ammonium chloride. The organic layer was washed with two 250 mL portions of an aqueous solution saturated with sodium bicarbonate, and dried with magnesium chloride. The mixture was filtered and the filtrate was concentrated under reduced pressure, yielding 56.4 grams of material. The material was distilled under reduced pressure, yielding 52.5 grams of 4-propoxyphenylmethyl chloride, bp 92 C/0.3 mm Hg.

Step B Synthesis of ethyl N-(4-propoxyphenylmethyl) piperidin-4-ylcarboxylate as an intermediate To a stirred solution of 47.5 grams (0.30 mole) of ethyl piperidin-4-ylcarboxylate in 70 mL (0.40 mole) of N, N-diisopropylethylamine was added dropwise a solution of 52.5 grams (0.29 mole) of 4-propoxyphenylmethyl chloride in 50 mL of dimethyl sulfoxide. The reaction caused the reaction mixture temperature to rise to about 35° C. Upon completion of the addition the reaction mixture was stirred for 30 minutes, warmed to 40° C., and then allowed to cool to ambient temperature. After this time the reaction mixture was poured into 500 mL of aqueous 10% ammonium chloride. The mixture was extracted with three 250 mL portions of diethyl ether, and the combined extracts were washed with two 250 mL portions of an aqueous solution saturated with ammonium chloride, one 250 mL portion of water, and one 250 mL portion of an aqueous solution saturated with sodium chloride. The organic layer was dried with magnesium sulfate and filtered. The filtrate was concentrated under reduced pressure, yielding 80.0 grams of ethyl N-(4-propoxyphenylmethyl)piperidin-4-ylcarboxylate. The NMR spectrum was consistent with the proposed structure.

Step C Synthesis of N-(4-propoxyphenylmethyl)-4-[bis(trifluoromethylphenyl)hydroxymethyl]piperidine (Compound 102)

This compound was prepared in a manner analogous to that of Step B of Example 2, with 1.5 grams (0.005 mole) of ethyl N-(4-propoxyphenylmethyl)piperidin-4-ylcarboxylate, 3.4 grams (0.015 mole) of 4-trifluoromethylphenyl bromide, and 0.4 gram (0.015 gram-atom) of magnesium turnings in 15 mL of tetrahydrofuran as reagents. The crude product was subjected to column chromatography on silica gel, with 1:1 ethyl acetate:heptane as the eluant. The product-containing fractions were combined and concentrated under reduced pressure, yielding 1.4 grams of N-(4-propoxyphenylmethyl)-4-[bis(trifluoromethylphenyl)hydroxymethyl]piperidine. The NMR spectrum was consistent with the proposed structure.

EXAMPLE 6

Synthesis of N-[4-(2-Ethylbenzoxazol-5-yl)methyl]-4-[bis(4-trifluoromethoxyphenyl)hydroxymethyl]piperidine Step A Synthesis of ethyl 3-nitro-4-hydroxybenzoate as an intermediate To a stirred solution of 20.0 grams (0.12 mole) of ethyl 4-hydroxybenzoate in 200 mL of acetic acid was added a solution of 7.5 mL (excess) of 70% nitric acid in 30 mL of acetic acid. After the reaction mixture stirred for about one hour, it gradually turned orange and warmed to about 40° C. The reaction mixture was stirred for an additional eighteen hours and then was poured into 800 mL of ice-water. The mixture was stirred until the ice melted, and filtered to collect a solid, which was dissolved in ethyl acetate and dried with magnesium sulfate. The mixture was filtered, and the filtrate was concentrated under reduced pressure, yielding 22.0 grams of ethyl 3-nitro-4-hydroxybenzoate, mp 70–71° C. The NMR spectrum was consistent with the proposed structure.

Step B Synthesis of ethyl (2-ethylbenzoxazol-5-yl)carboxylate as an intermediate A mixture of 10.4 grams (0.05 mole) of ethyl 3-nitro-4-hydroxybenzoate, 0.3 gram of platinum oxide (catalyst) in 200 mL of ethyl acetate was shaken in a Parr hydrogenator until the theoretical amount of hydrogen gas was taken up. The mixture was filtered to remove the catalyst, and the filtrate was concentrated under reduced pressure, yielding 9.6 grams of ethyl 3-amino-4-hydroxybenzoate as a solid. The NMR spectrum was consistent with the proposed structure. This 3-amino derivative, 9.0 grams (0.05 mole), was dissolved in 150 mL of ethanol and 9.7 grams (0.06 mole) of triethyl orthopropionate was added. The reaction mixture was heated at reflux for three hours, then cooled to ambient temperature and concentrated under reduced pressure to a residue. The residue was subjected to column chromatography on silica gel, with 1:4 ethyl acetate:heptane as the eluant. The product-containing fractions were combined and concentrated under reduced pressure, yielding 8.7 grams of ethyl (2-ethylbenzoxazol-5-yl)carboxylate, mp 35–37° C. The NMR spectrum was consistent with the proposed structure.

Step C Synthesis of (2-ethylbenzoxazol-5-yl)methanol as an intermediate

A stirred solution of 8.0 grams (0.037 mole) of ethyl (2-ethylbenzoxazol-5-yl)carboxylate in 100 mL of anhydrous tetrahydrofuran was cooled to 0° C., and 20 mL (0.02 mole) of a 1.0 molar solution of lithium aluminum hydride in tetrahydrofuran was added portionwise from a syringe. Upon completion of the addition the reaction mixture was stirred at 0° C. for 15 minutes, then was allowed to warm to ambient temperature, where it stirred for about 18 hours. The reaction mixture was poured into a mixture of 250 mL of an aqueous solution saturated with ammonium chloride and ice. The mixture was then extracted with two 250 mL portions of diethyl ether. The combined extracts were washed with an aqueous solution saturated with sodium chloride, dried with magnesium sulfate, and filtered. The filtrate was concentrated under reduced pressure to a residue, which was subjected to column chromatography on silica gel, with ethyl acetate as the eluant. The product-containing fractions were combined and concentrated under reduced pressure, yielding 4.1 grams of (2-ethylbenzoxazol-5-yl)methanol. The NMR spectrum was consistent with the proposed structure.

Step D Synthesis of ethyl N-(2-ethylbenzoxazol-5-ylmethyl)piperidin-4-ylcarboxylate as an intermediate To a stirred solution of 3.4 grams (0.019 mole) of (2-ethylbenzoxazol-5-yl)methanol in 25 mL of toluene was added 1.6 grams (0.006 mole) of phosphorous tribromide from a syringe. A precipitate formed immediately, and additional toluene was added to the reaction mixture to aid stirring. The reaction caused the reaction mixture temperature to rise to about 35° C. Upon completion of the addition, the reaction mixture stirred for an additional 20 minutes. The reaction mixture was then concentrated under reduced pressure to a residual solid. The solid was dissolved in 30 mL of dimethyl sulfoxide and, with stirring, 3.7 grams (0.029 mole) of N,N-diisopropylethylamine and 3.1 grams (0.019 mole) of ethyl piperdin-4-ylcarboxylate were added simultaneously from syringes. The resultant reaction caused the reaction mixture temperature to rise to about 40° C. The reaction mixture was allowed to cool to ambient temperature as it stirred for about 18 hours. The reaction mixture was poured into water and extracted with ethyl acetate and then with diethyl ether. The combined extracts were washed with an aqueous solution saturated with sodium bicarbonate, and then with an aqueous solution saturated with sodium chloride. The organic layer was concentrated under reduced pressure to a residual oil, which was subjected to column chromatography on silica gel, with ethyl acetate as the eluant. The product-containing fractions were combined and concentrated under reduced pressure, yielding 2.1 grams of ethyl N-(2-ethylbenzoxazol-5-ylmethyl)piperidin-4-ylcarboxylate. The NMR spectrum was consistent with the proposed structure.

Step E Synthesis of N-[4-(2-ethylbenzoxazol-5-yl)methyl]-4-[bis(4-trifluoromethoxyphenyl)hydroxymethyl]piperidine This compound was prepared in a manner analogous to that of Step B of Example 2, with 1.9 grams (0.006 mole) of ethyl N-(2-ethylbenzoxazol-5-ylmethyl)piperidin-4-ylcarboxylate, 3.6 grams (0.015 mole) of 4-trifluoromethoxyphenyl bromide, and 0.4 gram (0.015 gram-atom) of magnesium turnings in 35 mL of tetrahydrofuran as reagents. The crude reaction product was subjected to column chromatography on silica gel, with methylene chloride and then ethyl acetate as eluants. The product-containing fractions were combined and concentrated under reduced pressure, yielding 2.1 grams of N-[4-(2-ethylbenzoxazol-5-yl)methyl]-4-[bis(4-trifluoromethoxyphenyl)hydroxymethyl]piperidine. The NMR spectrum was consistent with the proposed structure.

EXAMPLE 7

Synthesis of N-[4-(2-methyl-2H-tetrazol-5-yl)phenylmethyl]-4-[bis(4-trifluoromethoxyphenyl)-hydroxymethyl]-piperidine (Compound 9)

Step A Synthesis of 4-(2-methyl-2H-tetrazol-5-yl)benzaldehyde as an intermediate A stirred solution of 2.2 grams (0.009 mole) 4-(2-methyl-2H-tetrazol-5-yl)phenyl bromide in 70 mL of dry tetrahydrofuran was cooled to −70° C., and 7.4 mL (0.018 mole) of n-butyllithium (2.5M in hexanes) was added dropwise from a syringe. The resulting reaction caused the reaction mixture temperature to rise to about −50° C. The reaction mixture was again cooled to −70° C., and stirring was continued for about 30 minutes. After this time 0.8 mL (0.010 mole) of N,N-dimethylformamide was added during a 90 second period. The reaction mixture was then stirred for 30 minutes at ice-water bath temperature, after which time it was allowed to warm to ambient temperature. The reaction mixture was poured into 200 mL of an aqueous solution saturated with ammonium chloride. The mixture was stirred for about 90 minutes and then extracted with three 150 mL portions of ethyl acetate. The combined extracts were washed with one 400 mL portion of an aqueous solution saturated with sodium chloride. The organic layer was dried with sodium sulfate and filtered. The filtrate was concentrated under reduced pressure to a residual oil, which was subjected to column chromatography on silica gel, with 3:7 ethyl acetate:heptane as the eluant. The product-containing fractions were combined and concentrated under reduced pressure, yielding 0.5 gram of 4(2-methyl-2H-tetrazol-5-yl)benzaldehyde. The NMR spectrum was consistent with the proposed structure.

Step B Synthesis of 4-(2-methyl-2H-tetrazol-5-yl)phenylmethanol as an intermediate This compound was prepared in a manner analogous to that of Step A of Example 5, with 0.5 gram (0.003 mole) of 4-(2-methyl-2H-tetrazol-5-yl)benzaldehyde and 0.1 gram (0.003 mole) of sodium borohydride in 17 mL of ethanol. The yield of 4-(2-methyl-2H-tetrazol-5-yl)phenylmethanol was about 0.4 gram. The NMR spectrum was consistent with the proposed structure.

Step C Synthesis of 4-(2-methyl-2H-tetrazol-5-yl)phenylmethyl bromide as an intermediate This compound was prepared in a manner analogous to that of Step D of Example 6, with 0.4 gram (0.002 mole) of 4-(2-methyl-2H-tetrazol-5-yl)phenylmethanol and 0.07 mL (0.0007 mole) of phosphorous tribromide in 7 mL of tetrahydrofuran as the reagents. The yield of 4-(2-methyl-2H-tetrazol-5-yl)phenylmethyl bromide was 0.7 gram, which was used in the next reaction without further characterization.

Step D Synthesis of N-[4-(2-methyl-2H-tetrazol-5-yl)phenylmethyl]-4-[bis(4-trifluoromethoxyphenyl)hydroxymethyl]piperidine (Compound 9)

This compound was prepared in a manner analogous to that of Step D of Example 4, with 0.3 gram (0.001 mole) of 4-(2-methyl-2H-tetrazol-5-yl)phenylmethyl bromide, 0.5 gram (0.001 mole) of 4-[bis(4-trifluoromethoxyphenyl)hydroxymethyl]piperidine (prepared as in Step C of Example 4), and 0.6 gram (0.004 mole) of N,N-diisopropylethylamine in about 5 mL of dimethyl sulfoxide as reagents. The crude reaction product was subjected to column chromatography on silica gel, with 3:7 acetone:methylene chloride as the eluant. The product-containing fractions were combined and concentrated under reduced pressure, yielding about 0.2 gram of N-[4-(2-methyl-2H-tetrazol-5-yl)phenylmethyl]-4-[bis(4-trifluoromethoxyphenyl)hydroxymethyl]piperidine. The NMR spectrum was consistent with the proposed structure.

EXAMPLE 8

Synthesis of N-[4(4,5-dihydro-1-methyl-5-oxo-1H-1,2,4-triazol-4-yl)phenylmethyl]-4-[bis(4-trifluoromethylphenyl)hydroxymethyl]piperidine (Compound 12)

Step A Synthesis of 4,5-dihydro-1-methyl-5-oxo4-(4-methylphenyl)-1H-1,2,4-triazole as an intermediate To a stirred solution of 3.5 grams (0.08 mole) of methylhydrazine in 50 mL of tetrahydrofuran, cooled to 0° C., was added dropwise 10.0 grams (0.08 mole) of 4-methylphenyl isocyanate. Upon completion of the addition the reaction mixture was stirred at 0° C. for 30 minutes, then allowed to warm to ambient temperature, where it stirred for one hour. After this time the reaction mixture was concentrated under reduced pressure to a residual solid. The solid was dissolved in 100 mL of dioxane and 11.1 grams (0.08 mole) of triethyl orthoformate and three drops of concentrated sulfuric acid were added. The reaction mixture was heated at reflux for about three hours, during which time about 75 mL of a water-dioxane azeotrope was collected by distillation, after which the reaction mixture was stirred at ambient temperature for about 60 hours. The reaction mixture was then concentrated under reduced pressure to a residual solid. The solid was dissolved in about 150 mL of ethyl acetate, and washed with one 50 mL portion of an aqueous solution saturated with sodium bicarbonate and one 50 mL portion of an aqueous solution saturated with sodium chloride. The organic layer was dried with magnesium sulfate and filtered. The filtrate was concentrated under reduced pressure to a residual solid, which was subjected to column chromatography on silica gel, with 3:7 ethyl acetate:heptane as the eluant. The product-containing fractions were combined and concentrated under reduced pressure, yielding 5.6 grams of an uncyclized intermediate of the intended product. This intermediate was then stirred with 10 mL of Eaton's Reagent (a 7.5% wt/wt solution of phosphorous pentoxide in methanesulfonic acid) for about 18 hours. The mixture was then poured into ice-water and the resultant precipitate collected by filtration, yielding 3.3 grams of 4,5-dihydro-1-methyl-5-oxo-4-(4-methylphenyl)-1H-1,2,4-triazole.

The NMR spectrum was consistent with the proposed structure.

Step B Synthesis of 4,5-dihydro-1-methyl-5-oxo-4-(4-bromomethylphenyl)-1H-1,2,4-triazole as an intermediate To a stirred solution of 2.6 grams (0.013 mole) of 4,5-dihydro-1-methyl-5-oxo-4-(4-methylphenyl)-1H-1,2,4-triazole in 150 mL of carbon tetrachloride were added 0.3 gram (catalyst) of benzoyl peroxide and 2.5 grams (0.014 mole) of N-bromosuccinimide. The reaction mixture was heated at reflux for three hours, after which it was cooled and concentrated under reduced pressure, yielding 2.6 grams of 4,5-dihydro-1-methyl-5-oxo-4-(4-bromomethylphenyl)-1H-1,2,4-triazole, which was used in the next reaction without further characterization.

Step C Synthesis of N-[4-(4,5dihydro-1-methyl-5-oxo-1H-1,2,4-triazol-4-yl)phenylmethyl]-4-[bis(4-trifluoromethylphenyl)hydroxymethyl]piperidine (Compound 12)

This compound was prepared in a manner analogous to that of Step D of Example 4, with 2.0 grams (0.007 mole) of 4,5-dihydro-1-methyl-5-oxo4-(4-bromomethylphenyl)-1H-1,2,4-triazole, 2.0 grams (0.005 mole) of 4-[bis(4-trifluoromethoxyphenyl)hydroxymethyl]piperidine (prepared as in Step C of Example 4), and 3.2 grams (0.025 mole) of N,N-diisopropylethylamine in about 15 mL of dimethyl sulfoxide as reagents. The crude reaction product was subjected to column chromatography on silica gel, with 2:8 heptane:ethyl acetate, and then pure ethyl acetate as eluants. The product-containing fractions were combined and concentrated under reduced pressure, yielding 1.6 grams of N-[4-(4,5-dihydro-1-methyl-5-oxo-1H-1,2,4-triazol-4-yl)phenylmethyl]-4-[bis(4-trifluoromethylphenyl) hydroxymethyl]piperidine. The NMR spectrum was consistent with the proposed structure.

EXAMPLE 9

Synthesis of N-[4-(2-methyl-2H-tetrazol-5-yl) phenylmethyl]-4-[bis(4-trifluoromethylphenyl) hydroxymethyl]piperidine (Compound 31)

This compound was prepared in the manner of Step E of Example 6, with 2.4 grams (0.007 mole) of ethyl N-[4-(2-methyl-2H-tetrazol-5-yl)phenylmethyl]piperidin-4-ylcarboxylate, 2.8 mL (0.019 mole) of 4-trifluoromethylphenyl bromide, and 0.4 gram (0.018 gram-atom) of magnesium turnings in 50 mL of tetrahydrofuran. The yield of N-[4-(2-methyl-2H-tetrazol-5-yl) phenylmethyl]-4-[bis(4-trifluoromethylphenyl) hydroxymethyl]piperidine was 2.0 grams. The NMR spectrum was consistent with the proposed structure.

EXAMPLE 10

Synthesis of N-[4-(2-methyl-2H-tetrazol-5-yl) phenylmethyl]-4-[bis(4-trifluoromethylphenyl)-hydroxymethyl]piperidine N-oxide (Compound 32)

A solution of 1.1 grams (0.002 mole) of N-[4-(2-methyl-2H-tetrazol-5-yl)phenylmethyl]-4-[bis(4-trifluoromethylphenyl)hydroxymethyl]piperidine (Compound 31-prepared in Example 9) in 100 mL of methylene chloride was stirred, and 0.6 gram (excess) of 50–85% 3-chloroperoxybenzoic acid was added. Upon completion of addition, the reaction mixture was stirred at ambient temperature for about one hour. After this time the reaction mixture was washed with an aqueous 10% solution of sodium hydroxide. The organic layer was dried with magnesium sulfate and filtered. The filtrate was concentrated under reduced pressure, yielding 1.0 gram of N-[4-(2-methyl-2H-tetrazol-5-yl)phenyl-methyl]-4-[bis(4-trifluoromethylphenyl)hydroxymethyl]piperidine N-oxide. The NMR spectrum was consistent with the proposed structure.

EXAMPLE 11

Synthesis of N-[4-(2-ethyl-2H-tetrazol-5-yl)phenyl-methyl]-4-[bis(2,2-difluoro-1,3-benzodioxol-5-yl) hydroxymethyl]-piperidine (Compound 118)

This compound was prepared in the manner of Step E of Example 6, with 3.4 grams (0.010 mole) of ethyl N-[4-(2-ethyl-2H-tetrazol-5-yl)phenylmethyl]piperidin-4-ylcarboxylate, 7.1 grams (0.030 mole) of 5-bromo-2,2-difluoro-1,3-benzodioxole, and 0.97 gram (0.040 gram-atom) of magnesium turnings in 50 mL of tetrahydrofuran. The yield of N-[4-(2-ethyl-2H-tetrazol-5-yl)phenylmethyl]-4-[bis(2,2-difluoro-1,3-benzodioxol-5-yl)hydroxymethyl] piperidine was about 2.0 grams, mp 79–81° C. The NMR spectrum was consistent with the proposed structure.

Representative compounds prepared by the methods exemplified above are listed in Table 1. Characterizing properties are given in Table 2.

Biological Data

Candidate insecticides were incorporated into an artificial diet for evaluation of insecticidal activity against the tobacco budworm (*Heliothis virescens* [Fabricius]) in the following manner. Stock solutions of test chemical in dimethyl sulfoxide, ranging from 50 micromolar to 0.005 micromolar, were prepared for each rate of application. One hundred microliters of each of the stock solutions was manually stirred into 50 mL of a molten (65–70° C.) wheat germ-based artificial diet. The 50 mL of molten diet containing the test chemical was poured evenly into twenty wells in the outer two rows on each side of a twenty-five well, five row plastic tray. (Each well in the tray was about 1 cm in depth, with an opening of 3 cm by 4 cm at the lip.) Molten diet containing only dimethyl sulfoxide at the levels used in the test chemical-treated diet was poured into the five wells in the third (center) row of the tray. Each tray therefore contained one test chemical at a single rate of application, together with an untreated control. The rates of application, expressed as the negative log of the molar concentration, and the corresponding concentrations of the stock solution prepared for each rate are shown below:

| Stock Solution | Rate of Application |
| --- | --- |
| 50 micromolar | 4 |
| 5 | 5 |
| 0.5 | 6 |
| 0.05 | 7 |
| 0.005 | 8 |

Single second instar tobacco budworm larvae, selected at a stage of growth at which they uniformly weigh about 5 mg each, were placed in each well. Upon completion of infestation, a sheet of clear plastic was heat-sealed over the top of the tray by use of a common household flat iron. The trays were held at 25° C. at 60% relative humidity for five days in a growth chamber. Lighting was set at 14 hours of light and 10 hours of darkness. After the 5-day exposure period, mortality counts were taken, and the surviving insects were weighed. From the weights of the surviving insects that fed on the treated diet as compared to those insects that fed on the untreated diet, the percent growth inhibition caused by each test chemical was determined. From these data, the negative log of the concentration of the test chemical that provided 50% growth inhibition ($pI_{50}$) was determined by linear regression, when possible, for each test chemical. Also, where possible, the negative log of the concentration of the test chemical that provided 50% mortality ($pLC_{50}$) was determined. Compounds 118 and 119 were tested in a similar manner in which the artificial diet was surface-treated with candidate insecticide rather than having the candidate insecticide incorporated into the diet.

Candidate insecticides with high p150 values from the diet test were tested for insecticidal activity in foliar evaluations against tobacco budworm, beet armyworm (*Spodoptera exigua* [Hubner]), and cabbage looper (*Trichoplusia ni* [Hubner]).

In these tests against tobacco budworm and beet armyworm, nine-day-old chick pea plants (*Cicer arietinum*) were sprayed at 20 psi to runoff on both upper and lower leaf surfaces with solutions of test chemical to provide application rates as high as 1000 ppm of test chemical. The solvent used to prepare the solutions of test chemical was 10% acetone or methanol (v/v) and 0.1% of the surfactant octylphenoxypolyethoxyethanol in distilled water. Four replicates, each containing one chick pea plant, for each rate of application of test chemical were sprayed. The treated plants were transferred to a hood, where they were kept until the spray had dried.

The four chick pea plants for each replicate treated with test chemical as described above were removed from their pots by cutting the stems just above the soil line. The excised leaves and stems from the four plants in each replicate were placed in individual 8-ounce paper cups, each containing a moistened filter paper. Five second-instar (6 days old) tobacco budworms or beet armyworms (7–8 days old) were counted into each cup, taking care not to cause injury. An opaque plastic lid was placed on each cup, which was then held in a growth chamber for a 96 hour exposure period at 25° C. and 50% relative humidity. At the end of the 96 hour exposure period the cups were opened, and the numbers of dead, moribund, and live insects were counted. Using the insect counts, the efficacy of the test chemical was expressed in percent control. Percent control is derived from the total number of dead insects (TD) plus the total number of moribund insects (TM) as compared to the total number of insects (TI) in the test:

$$\% \text{ Control} = \frac{TD + TM}{TI} \times 100$$

The condition of the test plants was also observed for phytotoxicity and for reduction of feeding damage as compared to an untreated control.

Foliar tests with cabbage looper were conducted in the same manner as described above, the difference being that pinto bean plants (*Phaseolus vulgaris*) were used in place of chick pea plants.

The compounds of the present invention were active in the diet test against the tobacco budworm. Over forty of the compounds listed in Table 1 exhibited $pI_{50}$ values of 6.0 or greater. Compounds 9, 15, 31–34, 43, 53, 54, 72, 73, 95, 96, 98–101, 103, and 104 all exhibited $pI_{50}$ values of 6.5 or greater. Table 3 gives the insecticidal activity data for compounds tested in the diet test.

The compounds of the present invention also showed good to excellent insecticidal activity in the foliar test against tobacco budworm, beet armyworm, and cabbage looper. It can be seen from Table 4 that many compounds provided 80% control or greater of one or more of the test insect species at an application rate of 100 ppm in the foliar test.

For insecticidal application, the active compounds are formulated into insecticidal compositions by admixture in insecticidally effective amount with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present insecticidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These insecticidal compositions may be applied either as water-diluted sprays, or dusts, or granules to the areas in which insect control is desired. These formulations may contain as little as 0.1%, 0.2% or 0.5% to as much as 95% or more by weight of active ingredient.

Dusts are free flowing admixtures of the active ingredients with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders are in the form of finely divided particles which disperse readily in water or other dispersant. The wettable powder is ultimately applied to the locus where insect control is desired either as a dry dust or as an emulsion in water or other liquid. Typical carriers for wettable powders include Fuller's earth, kaolin clays, silicas, and other highly absorbent, readily wet, inorganic diluents. Wettable powders normally are prepared to contain about 5–80% of active ingredient, depending on the absorbency of the carrier, and usually also contain a small amount of a wetting, dispersing, or emulsifying agent to facilitate dispersion. For example, a useful wettable powder formulation contains 80.8 parts of the insecticidal compound, 17.9 parts of Palmetto clay, and 1.0 part of sodium lignosulfonate and 0.3 part of sulfonated aliphatic polyester as wetting agents.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isophorone, or other non-volatile organic solvent. For insecticidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing, or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agents, when used, normally comprise from 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as carbon dioxide, propane, or butane, may also be used. Water-soluble or water-dispersible granules are also useful formulations for insecticidal application of the present compounds. Such granular formulations are free-flowing, non-dusty, and readily water-soluble or water-miscible. The soluble or dispersible granular formulations described in U.S. Pat. No. 3,920,442 are useful herein with the present insecticidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active insecticidal compounds of this invention may be formulated and/or applied with other insecticides, fungicides, nematicides, plant growth regulators, fertilizers, or other agricultural chemicals. In using an active compound of this invention, whether formulated alone or with other agricultural chemicals, to control insects, an effective amount and concentration of the active compound is applied to the locus where control is desired. The locus may be., e.g., the insects themselves, plants upon which the insects feed, or the insect habitat. When the locus is the soil, e.g., soil in which agricultural crops have been or will be planted, the composition of the active compound may be applied to and optionally incorporated into the soil. For most applications the effective amount may be as low as, e.g. about 10 to 500 g/ha, preferably about 100 to 250 g/ha.

It is apparent that various modifications may be made in the formulation and application of the compounds of this invention without departing from the inventive concepts herein as defined inventive concepts herein as defined in the claims.

TABLE 1

Insecticidal N-(substituted alkyl)-4-[di(substituted)hydroxymethyl]piperidines

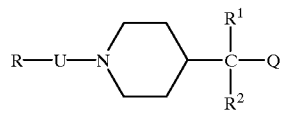

TABLE 1-continued

Insecticidal N-(substituted alkyl)-4-[di(substituted)hydroxymethyl]piperidines

Where R is a phenyl ring with substituents V, W, X, Y, Z; where V, W, Y, and Z are hydrogen Q is —OH, U is —(CH$_2$)$_n$—, n is 1, and;

R$^1$ and R$^2$ are 4-(trifluoromethoxy)phenyl (—C$_6$H$_4$—OCF$_3$)

| Cmpd No. | X |
|---|---|
| 1 | —OCH$_3$ |
| 2 (n = 2) | —OCH$_3$ |
| 3 | —NH(C=O)CH$_3$ |
| 4 | 1-methylpyrrol-3-yl |
| 5 | 2,5-dimethylpyrazol-1-yl (with CH$_3$ groups) |
| 6 | 5-methyl-1,2,4-oxadiazol-3-yl |
| 7 | 5-methyltetrazol-? (N—NH) |
| 8 | 1-methyl-1,2,3,4-tetrazol derivative with CH$_3$ |
| 9 | 1-methyl-1,2,3-triazol derivative with CH$_3$ |

23
TABLE 1-continued
Insecticidal N-(substituted alkyl)-4-
[di(substituted)hydroxymethyl]piperidines
10 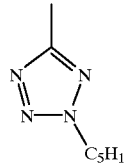
11 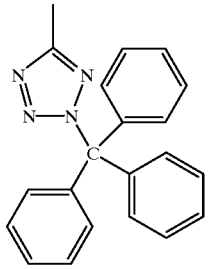
12 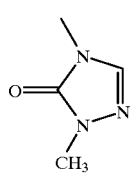
13 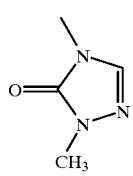
14 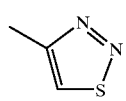
15 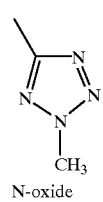
16 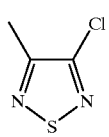
17 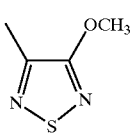
Where U is —(CH$_2$)$_n$—, and n is 1; Q is —OH;
24
TABLE 1-continued
Insecticidal N-(substituted alkyl)-4-
[di(substituted)hydroxymethyl]piperidines
R is 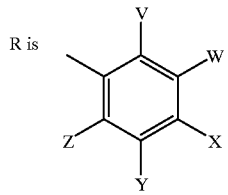 where V, W, Y, and Z are hydrogen; and
R$^1$ and R$^2$ are 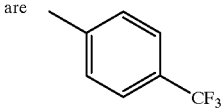
| Cmpd. No. | X |
| --- | --- |
| 18 | 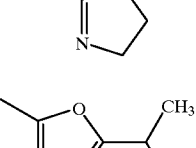 |
| 19 | 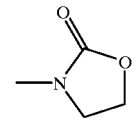 |
| 20 | 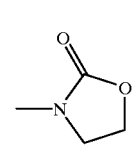 |
| 21 | 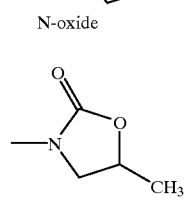 |
| 22 | 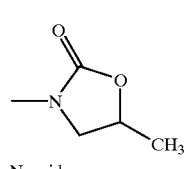 |
| 23 | 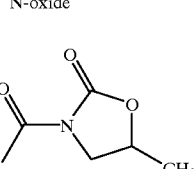 |
| 24 | 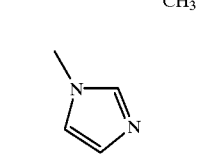 |
| 25 | |

TABLE 1-continued
Insecticidal N-(substituted alkyl)-4-[di(substituted)hydroxymethyl]piperidines
| | |
|---|---|
| 26 | 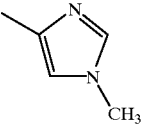 |
| 27 | 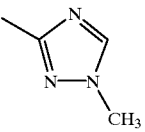 |
| 28 | 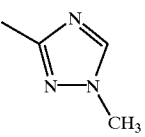<br>N-oxide |
| 29 | 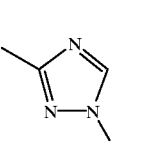 |
| 30 | 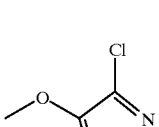<br>N-oxide |
| 31 | 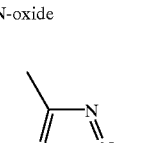 |
| 32 | 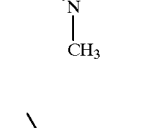<br>N-oxide |
| 33 | 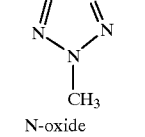 |
| 34 | 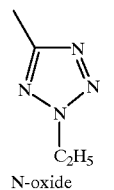<br>N-oxide |
| 35 | 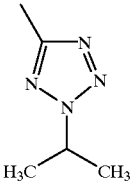 |
| 36 | 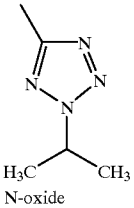<br>N-oxide |
| 37 | 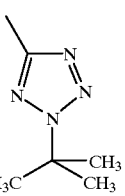 |
| 38 | 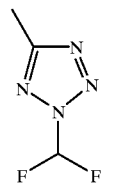 |
| 39 | 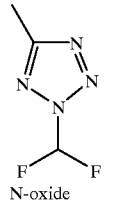<br>N-oxide |
| 40 | 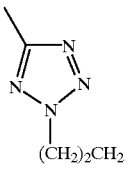 |

TABLE 1-continued
Insecticidal N-(substituted alkyl)-4-[di(substituted)hydroxymethyl]piperidines
41 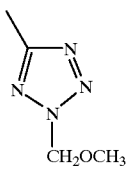
42 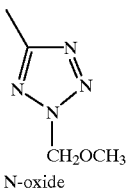
N-oxide
43 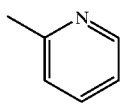
44 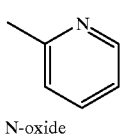
N-oxide
45 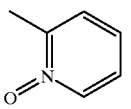
46 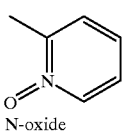
N-oxide
47 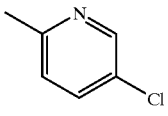
48 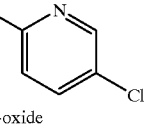
N-oxide
49 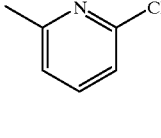
50 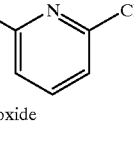
N-oxide
TABLE 1-continued
Insecticidal N-(substituted alkyl)-4-[di(substituted)hydroxymethyl]piperidines
51 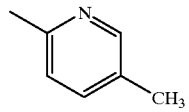
52 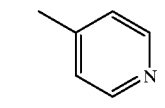
53 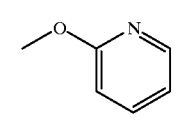
54 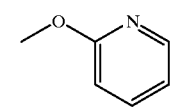
N-oxide
55 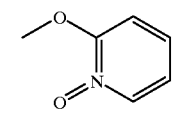
56 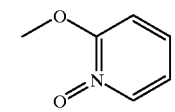
N-oxide
57 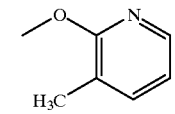
58 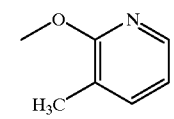
N-oxide
59 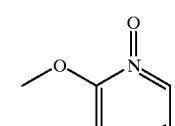
60 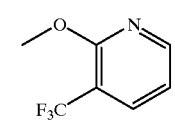
61 
N-oxide TABLE 1-continued
Insecticidal N-(substituted alkyl)-4-
[di(substituted)hydroxymethyl]piperidines
| 62 | 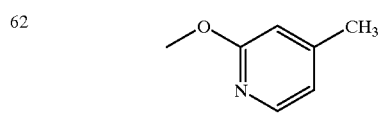 |
| 63 | 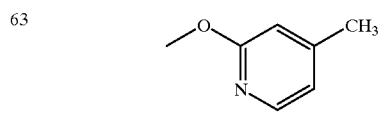 N-oxide |
| 64 | 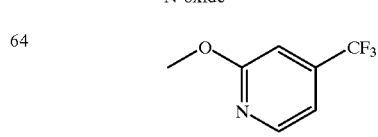 |
| 65 | 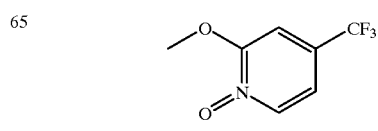 |
| 66 | 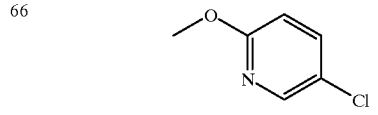 |
| 67 | 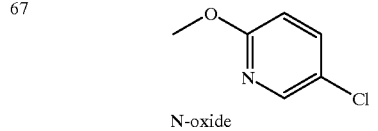 N-oxide |
| 68 | 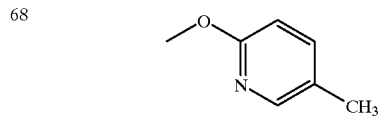 |
| 69 | 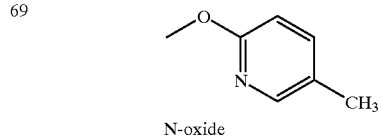 N-oxide |
| 70 | 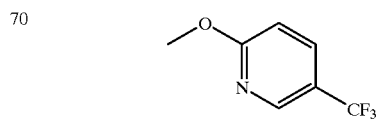 |
| 71 | 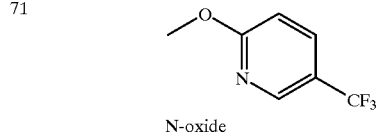 N-oxide |
| 72 | 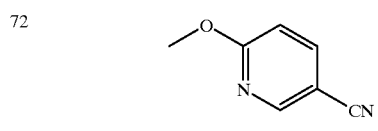 |
TABLE 1-continued
Insecticidal N-(substituted alkyl)-4-
[di(substituted)hydroxymethyl]piperidines
| 73 | 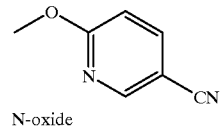 N-oxide |
| 74 | 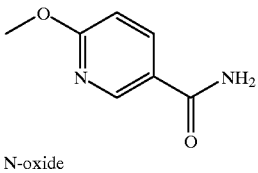 N-oxide |
| 75 | 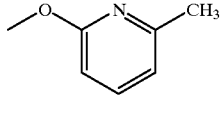 |
| 76 | 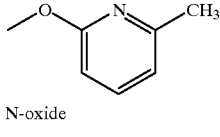 N-oxide |
| 77 | 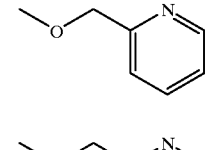 N-oxide |
| 78 | 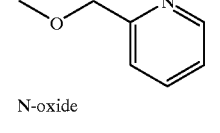 |
| 79 | 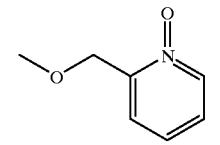 N-oxide |
| 80 | 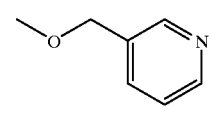 N-oxide |
| 81 | 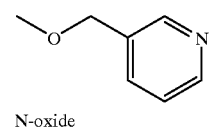 |
| 82 | 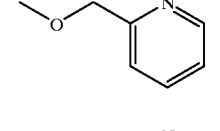 N-oxide |

TABLE 1-continued
Insecticidal N-(substituted alkyl)-4-
[di(substituted)hydroxymethyl]piperidines
| 83 | 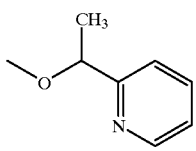 |
| 84 | 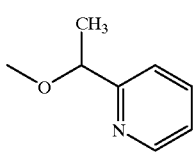 N-oxide |
| 85 | 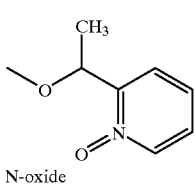 N-oxide |
| 86 | 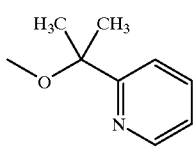 |
| 87 | 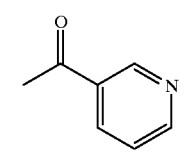 |
| 88 | 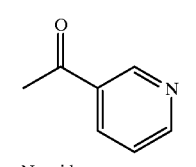 N-oxide |
| 89 | 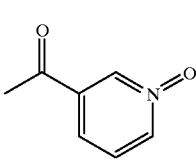 N-oxide |
| 90 | 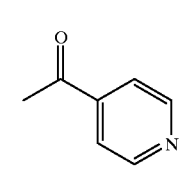 |
TABLE 1-continued
Insecticidal N-(substituted alkyl)-4-
[di(substituted)hydroxymethyl]piperidines
| 91 | 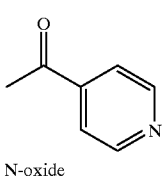 N-oxide |
| 92 | 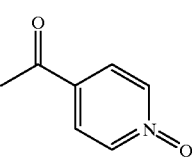 |
| 93 | 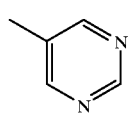 |
| 94 | 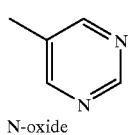 N-oxide |
| 95 | 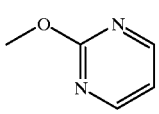 |
| 96 | 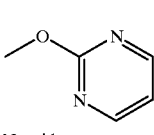 N-oxide |
| 97 | 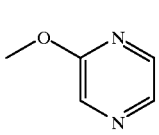 |
| 98 | 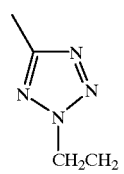 |
| 99 | 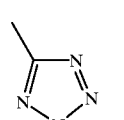 N-oxide |
| 100 | 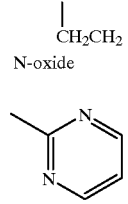 |

TABLE 1-continued

Insecticidal N-(substituted alkyl)-4-[di(substituted)hydroxymethyl]piperidines

| Cmpd. No. | Structure/Description |
|---|---|
| 101 | 2-methylpyrimidinyl N-oxide |
| 102 | —OC₃H₇ |

Where Q is —OH;, U is —(CH₂)ₙ—, where n is 1; and

R is (phenyl with V, W, Y, Z positions and X substituent) where V, W, Y and Z are hydrogen

| Cmpd. No. | X | R¹ | R² |
|---|---|---|---|
| 103 | 2-(1,3-dioxolan-2-yl) | 2-OCF₃-phenyl | 4-OCF₃-phenyl |
| 104 | 2-ethyl-2H-tetrazol-5-yl | 6-methyl-5-CF₃-pyridin-3-yl | 6-methyl-5-CF₃-pyridin-3-yl |

Where U is —(CH₂)ₙ—, and n is 1; Q is —OH;

R is (phenyl) where V, W, Y, and Z are hydrogen; and

R¹ and R² are 4-CF₃-phenyl

| Cmpd. No. | X |
|---|---|
| 105 | 6-methyl-2-ethylpyridinyl |
| 106 | 6-methyl-2-chloropyridinyl |
| 107 | 2-methyl-4-ethylpyrimidinyl |
| 108 | 2-methyl-4-chloropyrimidinyl |
| 109 | 3-methyl-1-ethylpyrazolyl |

$$R-U-N\text{(piperidine)}-C(R^1)(R^2)-Q$$

Q is OH, U is —(CH₂)ₙ—; n is 1

R is (phenyl with X substituent) where V, W, Y, and Z are hydrogen

| Cmpd No. | X | R¹ and R² | N-oxide |
|---|---|---|---|
| 110 | 2-methyl-2H-tetrazol-5-yl | 4-pentafluorothiophenyl | |
| 111 | 2-methyl-2H-tetrazol-5-yl | 4-pentafluorothiophenyl | x |
| 112 | 2-ethyl-2H-tetrazol-5-yl | 4-pentafluorothiophenyl | |
| 113 | 2-methyl-2H-tetrazol-5-yl | 4-pentafluorothiophenyl | x |
| 114 | 2-(2-fluoroethyl)-2H-tetrazol-5-yl | 4-pentafluorothiophenyl | |
| 115 | 2-(2-fluoroethyl)-2H-tetrazol-5-yl | 4-pentafluorothiophenyl | x |
| 116 | 2-methyl-2H-tetrazol-5-yl | 2,2-difluoro-1,3-benzodioxol-5-yl | |
| 117 | 2-methyl-2H-tetrazol-5-yl | 2,2-difluoro-1,3-benzodioxol-5-yl | x |
| 118 | 2-ethyl-2H-tetrazol-5-yl | 2,2-difluoro-1,3-benzodioxol-5-yl | |
| 119 | 2-ethyl-2H-tetrazol-5-yl | 2,2-difluoro-1,3-benzodioxol-5-yl | x |
| 120 | 2-(2-fluoroethyl)-2H-tetrazol-5-yl | 2,2-difluoro-1,3-benzodioxol-5-yl | |
| 121 | 2-(2-fluoroethyl)-2H-tetrazol-5-yl | 2,2-difluoro-1,3-benzodioxol-5-yl | x |
| 122 | 2-methyl-2H-tetrazol-5-yl | 2,2-difluoro-1,3-dioxolino[4,5-b]-pyrid-5-yl | |
| 123 | 2-methyl-2H-tetrazol-5-yl | 2,2-difluoro-1,3-dioxolino[4,5-b]-pyrid-5-yl | x |
| 124 | 2-ethyl-2H-tetrazol-5-yl | 2,2-difluoro-1,3-dioxolino[4,5-b]-pyrid-5-yl | |
| 125 | 2-ethyl-2H-tetrazol-5-yl | 2,2-difluoro-1,3-dioxolino[4,5-b]-pyrid-5-yl | x |
| 126 | 2-(2-fluoroethyl)-tetrazol-5-yl | 2,2-difluoro-1,3-dioxolino[4,5-b]-pyrid-5-yl | |
| 127 | 2-(2-fluoroethyl)-tetrazol-5-yl | 2,2-difluoro-1,3-dioxolino[4,5-b]-pyrid-5-yl | x |
| 128 | 2-methyl-2H-tetrazol-5-yl | 4-trifluoromethylthiophenyl | |

TABLE 1-continued

Insecticidal N-(substituted alkyl)-4-[di(substituted)hydroxymethyl]piperidines

| | | | |
|---|---|---|---|
| 129 | 2-methyl-2H-tetrazol-5-yl | 4-trifluoromethylthiophenyl | |
| 130 | 2-ethyl-2H-tetrazol-5-yl | 4-trifluoromethylthiophenyl | |
| 131 | 2-ethyl-2H-tetrazol-5-yl | 4-trifluoromethylthiophenyl | x |
| 132 | 2-(2-fluoroethyl)-2H-tetrazol-5-yl | 4-trifluoromethylthiophenyl | |
| 133 | 2-(2-fluoroethyl)-2H-tetrazol-5-yl | 4-trifluoromethylthiophenyl | x |
| 134 | 2-methyl-2H-tetrazol-5-yl | 4-trifluoromethylsulfinyl-phenyl | |
| 135 | 2-methyl-2H-tetrazol-5-yl | 4-trifluoromethylsulfinyl-phenyl | x |
| 136 | 2-ethyl-2H-tetrazol-5-yl | 4-trifluoromethylsulfinyl-phenyl | |
| 137 | 2-ethyl-2H-tetrazol-5-yl | 4-trifluoromethylsulfinyl-phenyl | x |
| 138 | 2-(2-fluoroethyl)-2H-tetrazol-5-yl | 4-trifluoromethylsulfinyl-phenyl | |
| 139 | 2-(2-fluoroethyl)-2H-tetrazol-5-yl | 4-trifluoromethylsulfinyl-phenyl | x |
| 140 | 2-methyl-2H-tetrazol-5-yl | 4-trifluoromethylsulfonyl-phenyl | |
| 141 | 2-methyl-2H-tetrazol-5-yl | 4-trifluoromethylsulfonyl-phenyl | x |
| 142 | 2-ethyl-2H-tetrazol-5-yl | 4-trifluoromethylsulfonyl-phenyl | |
| 143 | 2-ethyl-2H-tetrazol-5-yl | 4-trifluoromethylsulfonyl-phenyl | x |
| 144 | 2-(2-fluoroethyl)-2H-tetrazol-5-yl | 4-trifluoromethylsulfonyl-phenyl | |
| 145 | 2-(2-fluoroethyl)-2H-tetrazol-5-yl | 4-trifluoromethylsulfonyl-phenyl | x |
| 146 | 2-methyl-2H-tetrazol-5-yl | 5-pentafluorothiopyrid-2-yl | |
| 147 | 2-methyl-2H-tetrazol-5-yl | 5-pentafluorothiopyrid-2-yl | x |
| 148 | 2-ethyl-2H-tetrazol-5-yl | 5-pentafluorothiopyrid-2-yl | |
| 149 | 2-ethyl-2H-tetrazol-5-yl | 5-pentafluorothiopyrid-2-yl | x |
| 150 | 2-(2-fluoroethyl)-2H-tetrazol-5-yl | 5-pentafluorothiopyrid-2-yl | |
| 151 | 2-(2-fluoroethyl)-2H-tetrazol-5-yl | 5-pentafluorothiopyrid-2-yl | x |
| 152 | pyrid-2-yl | 4-pentafluorothiophenyl | |
| 153 | pyrid-2-yl | 4-pentafluorothiophenyl | x |
| 154 | pyrid-2-yl | 2,2-difluoro-1,3-benzo-dioxol-5-yl | |
| 155 | pyrid-2-yl | 2,2-difluoro-1,3-benzo-dioxol-5-yl | x |
| 156 | pyrid-2-yl | 2,2-difluoro-1,3-dioxolino-[4,5-b]-pyrid-5-yl | |
| 157 | pyrid-2-yl | 2,2-difluoro-1,3-dioxolino-[4,5-b]-pyrid-5-yl | x |
| 158 | pyrid-2-yl | 4-trifluoromethylthiophenyl | |
| 159 | pyrid-2-yl | 4-trifluoromethylthiophenyl | x |
| 160 | pyrid-2-yl | 4-trifluoromethylsulfinyl-phenyl | |
| 161 | pyrid-2-yl | 4-trifluoromethylsulfinyl-phenyl | x |
| 162 | pyrid-2-yl | 4-trifluoromethylsulfonyl-phenyl | |
| 163 | pyrid-2-yl | 4-trifluoromethylsulfonyl-phenyl | x |
| 164 | pyrid-2-yl | 5-pentafluorothiopyrid-2-yl | |
| 165 | pyrid-2-yl | 5-pentafluorothiopyrid-2-yl | x |
| 166 | pyrid-2-yloxy | 4-pentafluorothiophenyl | |
| 167 | pyrid-2-yloxy | 4-pentafluorothiophenyl | x |
| 168 | pyrid-2-yloxy | 2,2-difluoro-1,3-benzo-dioxol-5-yl | |
| 169 | pyrid-2-yloxy | 2,2-difluoro-1,3-benzo-dioxol-5-yl | x |
| 170 | pyrid-2-yloxy | 2,2-difluoro-1,3-dioxolino-[4,5-b]-pyrid-5-yl | |
| 171 | pyrid-2-yloxy | 2,2-difluoro-1,3-dioxolino-[4,5-b]-pyrid-5-yl | x |
| 172 | pyrid-2-yloxy | 4-trifluoromethylthiophenyl | |
| 173 | pyrid-2-yloxy | 4-trifluoromethylthiophenyl | x |
| 174 | pyrid-2-yloxy | 4-trifluoromethylsulfinyl-phenyl | |
| 175 | pyrid-2-yloxy | 4-trifluoromethylsulfinyl-phenyl | |
| 176 | pyrid-2-yloxy | 4-trifluoromethylsulfonyl-phenyl | |
| 177 | pyrid-2-yloxy | 4-trifluoromethylsulfonyl-phenyl | x |
| 178 | pyrid-2-yloxy | 5-pentafluorothiopyrid-2-yl | |
| 179 | pyrid-2-yloxy | 5-pentafluorothiopyrid-2-yl | x |
| 180 | pyrimidin-2-yl | 4-pentafluorothiophenyl | |
| 181 | pyrimidin-2-yl | 4-pentafluorothiophenyl | x |
| 182 | pyrimidin-2-yl | 2,2-difluoro-1,3-benzo-dioxol-5-yl | |
| 183 | pyrimidin-2-yl | 2,2-difluoro-1,3-benzo-dioxol-5-yl | x |
| 184 | pyrimidin-2-yl | 2,2-difluoro-1,3-dioxolino-[4,5-b]-pyrid-5-yl | |
| 185 | pyrimidin-2-yl | 2,2-difluoro-1,3-dioxolino-[4,5-b]-pyrid-5-yl | x |
| 186 | pyrimidin-2-yl | 4-trifluoromethylthiophenyl | |
| 187 | pyrimidin-2-yl | 4-trifluoromethylthiophenyl | x |
| 188 | pyrimidin-2-yl | 4-trifluoromethylsulfinyl-phenyl | |
| 189 | pyrimidin-2-yl | 4-trifluoromethylsulfinyl-phenyl | x |
| 190 | pyrimidin-2-yl | 4-trifluoromethylsulfonyl-phenyl | |
| 191 | pyrimidin-2-yl | 4-trifluoromethylsulfonyl-phenyl | x |
| 192 | pyrimidin-2-yl | 5-pentafluorothiopyrid-2-yl | |
| 193 | pyrimidin-2-yl | 5-pentafluorothiopyrid-2-yl | x |
| 194 | pyrimidin-2-yloxy | 4-pentafluorothiophenyl | |
| 195 | pyrimidin-2-yloxy | 4-pentafluorothiophenyl | x |
| 196 | pyrimidin-2-yloxy | 2,2-difluoro-1,3-benzo-dioxol-5-yl | |
| 197 | pyrimidin-2-yloxy | 2,2-difluoro-1,3-benzo-dioxol-5-yl | x |
| 198 | pyrimidin-2-yloxy | 2,2-difluoro-1,3-dioxolino-[4,5-b]-pyrid-5-yl | |
| 199 | pyrimidin-2-yloxy | 2,2-difluoro-1,3-dioxolino-[4,5-b]-pyrid-5-yl | x |
| 200 | pyrimidin-2-yloxy | 4-trifluoromethylthiophenyl | |
| 201 | pyrimidin-2-yloxy | 4-trifluoromethylthiophenyl | x |
| 202 | pyrimidin-2-yloxy | 4-trifluoromethylsulfinyl-phenyl | |
| 203 | pyrimidin-2-yloxy | 4-trifluoromethylsulfinyl-phenyl | x |
| 204 | pyrimidin-2-yloxy | 4-trifluoromethylsulfonyl-phenyl | |
| 205 | pyrimidin-2-yloxy | 4-trifluoromethylsulfonyl-phenyl | x |
| 206 | pyrimidin-2-yloxy | 5-pentafluorothiopyrid-2-yl | |
| 207 | pyrimidin-2-yloxy | 5-pentafluorothiopyrid-2-yl | x |

TABLE 2

Characterizing Data

| | |
|---|---|
| 1 | 86–96° C. |
| 2 | GEL |
| 3 | OIL |
| 4 | OIL |
| 5 | FOAM |
| 6 | FOAM |
| 7 | 240 DEC |
| 8 | FQAM |
| 9 | OIL |
| 10 | OIL |
| 11 | FOAM |
| 12 | FOAM |
| 13 | FOAM |
| 14 | SEMI-SOLID |
| 15 | 165–170 C |
| 18 | 90–95 |
| 19 | 91–94 |

TABLE 2-continued

Characterizing Data

| | |
|---|---|
| 20 | 125–128 |
| 21 | 226–228 |
| 22 | 118–121 |
| 23 | 200–202 |
| 24 | 94–100 |
| 25 | WHITE SOLID |
| 26 | 110–120 |
| 27 | 98–102 |
| 28 | 203 DEC |
| 29 | OIL |
| 30 | 188–190 |
| 31 | 57–62 |
| 32 | >200 |
| 33 | 60–65 |
| 34 | >210 |
| 35 | WHITE FOAM |
| 36 | FOAM |
| 37 | 77–80 |
| 38 | 70–74 |
| 39 | 142–148 |
| 40 | 65–67 |
| 41 | OIL |
| 42 | 210–211 |
| 43 | 75–89 |
| 44 | 198–202 |
| 45 | 115–125 DEC |
| 46 | 171–191 DEC |
| 47 | 88–91 C |
| 48 | 214–215 DEC |
| 49 | 80–85 C |
| 50 | 212–215 DEC |
| 51 | 78–87 |
| 52 | 114–118 DEC |
| 53 | 71–77 |
| 54 | 208–210 |
| 55 | 104–120 DEC |
| 56 | 166–186 DEC |
| 57 | 78–82 |
| 58 | 209–213 |
| 59 | 105–110 |
| 60 | 77–83 |
| 61 | 208–212 DEC. |
| 62 | SOLID |
| 63 | SOLID |
| 64 | SOLID |
| 65 | 105–113 |
| 66 | SOLID |
| 67 | SOLID |
| 68 | 72–77 |
| 69 | 153–159 |
| 70 | 69–77 |
| 71 | 215–220 DEC |
| 72 | 82–85 |
| 73 | 216–220 DEC |
| 74 | 179–182 |
| 75 | 73–77 |
| 76 | 144–145 |
| 77 | 170–174 |
| 78 | 61–68 |
| 79 | 199–204 DEC |
| 80 | 214–217 DEC |
| 81 | 54–68 |
| 82 | 210–215 DEC |
| 83 | 51–55 |
| 84 | 143–147 |
| 85 | 155–170 |
| 86 | 65–75 |
| 87 | SOLID |
| 88 | 188–194 |
| 89 | 166–171 |
| 90 | 80–88 |
| 91 | 185–192 |
| 92 | 203–206 |
| 93 | 187–189 |
| 94 | 199–203 |
| 95 | 88–94 |
| 96 | 185–197 DEC |
| 97 | SOLID |
| 98 | SOLID |
| 99 | SOLID |
| 100 | SOLID |
| 101 | SOLID |
| 102 | FOAM |
| 103 | GUMMY FOAMY SOLID |
| 104 | SOLID |
| 118 | 79–81 |
| 119 | 185–187 |

TABLE 3

Insecticidal Activity When Incorporated into the Diet of Tobacco Budworm

| Cmpd. No. | Rate of Application[1] | Percent Growth Inhibition[2,3] | $pI_{50}$[4] | Percent Mortality[5] | $pLC_{50}$[6] |
|---|---|---|---|---|---|
| 1 | 4 | 100* | 6.1* | 100* | 4.6* |
| 2 | 4 | 98 | 5.6 | 25 | <4.0 |
| 3 | 4 | 95 | 4.7 | 0 | — |
| 4 | 4 | 100* | 5.5* | 100* | 5.5* |
| 5 | 4 | 100 | 5.5 | 100 | 4.6 |
| 6 | 4 | 100 | 6.0 | 100 | 5.1 |
| 7 | 4 | 92* | 5.0* | 0* | — |
| 8 | 4 | 79* | 4.5* | 0* | — |
| 9 | 4 | 100 | 6.6 | 100 | 5.6 |
| 10 | 4 | 49* | 4.0 | 0* | — |
| 11 | 3.5 | 2 | — | 0 | — |
| 12 | 4 | 98 | 5.4 | 35 | <4.0 |
| 13 | 4 | 98 | 5.4 | 30 | <4.0 |
| 14 | 4 | 99 | 5.5 | 100 | 4.5 |
| 15 | 4 | 100 | 6.6 | 100 | 5.9 |
| 18 | 4 | 73 | 4.2 | 0 | NM |
| 19 | 4 | 98 | 4.5 | 90 | 4.4 |
| 20 | 4 | 93 | 5.3 | 10 | <3.5 |
| 21 | 4 | 95 | 5.0 | 10 | <3.5 |
| 22 | 4 | 99 | 5.5 | 35 | 3.9 |
| 23 | 4 | 100 | 5.5 | 65 | 4.2 |
| 24 | 4 | 86 | 4.5 | 0 | <3.5 |
| 25 | 4 | 33 | 3.8 | 0 | NM |
| 26 | 4 | 90 | 5.2 | 15 | NM |
| 27 | 4 | 100 | 6.2 | 100 | 5.5 |
| 28 | 4 | 100 | 5.6 | 100 | 5.1 |
| 29 | 4 | 98 | 5.2 | 60 | 4.2 |
| 30 | 4 | 98 | 5.1 | 40 | <4.0 |
| 31 | 4 | 100 | 6.5 | 100 | 5.6 |
| 32 | 4 | 100 | 6.5 | 100 | 5.6 |
| 33 | 4 | 99 | 6.6 | 100 | 6.1 |
| 34 | 4 | 100 | 6.5 | 100 | 5.9 |
| 35 | 4 | 100 | 6.4 | 100 | 5.5 |
| 36 | 4 | 100 | 6.1 | 100 | 5.4 |
| 37 | 4 | 100 | 5.5 | 100 | 5.4 |
| 38 | 4 | 100 | 6.2 | 100 | 5.6 |
| 39 | 4 | 100 | 6.0 | 100 | 5.5 |
| 40 | 4 | 100 | 6.2 | 100 | 5.4 |
| 41 | 4 | 100 | 6.5 | 100 | 5.4 |
| 42 | 4 | 100 | 6.4 | 100 | 5.8 |
| 43 | 4 | 100 | 6.5 | 100 | 5.5 |
| 44 | 4 | 100 | 6.2 | 100 | 5.5 |
| 45 | 4 | 100 | 5.9 | 100 | 5.3 |
| 46 | 4 | 100 | 5.5 | 100 | 4.9 |
| 47 | 4 | 100 | 4.5 | 100 | 4.5 |
| 48 | 4 | 98 | 4.8 | 85 | 4.4 |
| 49 | 4 | 100 | 6.4 | 100 | 5.9 |
| 50 | 4 | 100 | 6.4 | 100 | 5.5 |
| 51 | 4 | 100 | 6.1 | 100 | 5.4 |
| 52 | 4 | 80 | 4.8 | 0 | NM |
| 53 | 4 | 100* | 6.6* | 100* | 5.9* |
| 54 | 4 | 100 | 6.5 | 100 | 5.5 |
| 55 | 4 | 100 | 5.5 | 55 | 4.1 |

TABLE 3-continued

Insecticidal Activity When Incorporated into the Diet of Tobacco Budworm

| Cmpd. No. | Rate of Application[1] | Percent Growth Inhibition[2,3] | $pI_{50}$[4] | Percent Mortality[5] | $pLC_{50}$[6] |
|---|---|---|---|---|---|
| 56 | 4 | 100 | 5.5 | 100 | 4.5 |
| 57 | 4 | 100 | 6.1 | 100 | 5.1 |
| 58 | 4 | 100 | 6.0 | 100 | 5.0 |
| 59 | 4 | 100 | 5.0 | 100 | 4.5 |
| 60 | 4 | 100 | 6.4 | 100 | 5.9 |
| 61 | 4 | 100 | 6.5 | 100 | 5.5 |
| 62 | 4 | 100 | 6.2 | 100 | 5.2 |
| 63 | 4 | 100 | 5.9 | 100 | 4.9 |
| 64 | 4 | 100 | 6.0 | 100 | 5.1 |
| 65 | 4 | 97 | 5.2 | 25 | <4.0 |
| 66 | 4 | 100 | 6.4 | 100 | 5.4 |
| 67 | 4 | 100 | 6.0 | 70 | 4.3 |
| 68 | 4 | 100 | 5.7 | 90 | 4.4 |
| 69 | 4 | 91 | 5.3 | 100 | 4.5 |
| 70 | 4 | 100 | 5.9 | 100 | 4.9 |
| 71 | 4 | 100 | 5.7 | 100 | 4.6 |
| 72 | 4 | 100 | 6.6 | 100 | 5.5 |
| 73 | 4 | 100 | 6.6 | 100 | 5.5 |
| 74 | 4 | 16 | NM | 0 | NM |
| 75 | 4 | 100 | 6.3 | 100 | 5.4 |
| 76 | 4 | 100 | 6.2 | 100 | 5.2 |
| 77 | 4 | 98 | 5.1 | 60 | 4.2 |
| 78 | 4 | 100 | 6.0 | 100 | 4.5 |
| 79 | 4 | 100 | 6.0 | 100 | 4.5 |
| 80 | 4 | 96 | 5.2 | 15 | NM |
| 81 | 4 | 93 | 4.5 | 20 | NM |
| 82 | 4 | 93 | 4.7 | 25 | <4.0 |
| 83 | 4 | 100 | 6.0 | 100 | 4.5 |
| 84 | 4 | 100 | 6.0 | 100 | 4.6 |
| 85 | 4 | 88 | 5.2 | 0 | NM |
| 86 | 4 | 95 | 6.1 | 30 | <4.0 |
| 87 | 4 | 75 | 4.4 | 5 | NM |
| 88 | 4 | 74 | 4.6 | 10 | NM |
| 89 | 4 | 44 | <4.0 | 0 | NM |
| 90 | 4 | 38 | <4.0 | 10 | NM |
| 91 | 4 | 74 | 4.3 | 0 | NM |
| 92 | 4 | 43 | <4.0 | 20 | NM |
| 93 | 4 | 93 | 4.9 | 0 | NM |
| 94 | 4 | 88 | 4.7 | 0 | NM |
| 95 | 4 | 100 | 6.5 | 100 | 5.5 |
| 96 | 4 | 100 | 6.5 | 100 | 5.6 |
| 97 | 4 | 100 | 5.2 | 0 | NM |
| 98 | 4 | 100 | 6.6 | 100 | 6.5 |
| 99 | 4 | 100 | 6.5 | 100 | 6.4 |
| 100 | 4 | 100 | 6.5 | 100 | 6.4 |
| 101 | 4 | 100 | 6.5 | 100 | 5.4 |
| 102 | 4 | 100 | >6.0 | 100 | 5.5 |
| 103 | 4 | 100 | 6.5 | 100 | 4.9 |
| 104 | 4 | 100 | 6.8 | 100 | 6.4 |
| 118** | 4.6 | 100 | >6.6 | 100 | 6.1 |
| 119** | 4.6 | 100 | 6.1 | 100 | 6.0 |

[1] The rate of application is expressed as the negative log of the molar concentration of the test compound in the diet.
[2] Percent growth inhibition is derived from the total weight of the insects (IW) at each rate of application in the test relative to the total weight of the insects in an untreated control:

$$\% \text{ Gr. Inh} = \frac{[IW(control) - IW(test)]}{[IW(control)]} \times 100$$

[3] A minus % growth inhibition indicates that the insects weighed more at the termination of the test than those in the untreated control.
[4] $pI_{50}$ is the negative log of the concentration of the test chemical that provides 50% growth inhibition in the test species.
[5] Percent mortality is derived from the number of dead insects (TD) relative to the number of insects (TI) used in the test $$\% \text{ Mortality} = \frac{TD}{TI} \times 100$$

[6] $pLC_{50}$ is the negative log of the concentration of the test chemical that provides 50% mortality of the test insects.
*Average of more than one test.
NM is not measured.

**The artificial diet was surface-treated with candidate insecticide rather than having the candidate insecticide incorporated into the diet.

TABLE 4

Insecticidal Activity When Applied as Foliar Sprays

| Cmpd No. | Rate of Application (ppm) | Percent Control[1] | | |
|---|---|---|---|---|
| | | TBW[2] | CL[3] | BAW[4] |
| 1 | 100 | 80 | 100 | 55 |
| 4 | 100 | 59 | 70 | 30 |
| 9 | 100 | 100 | 100 | 100 |
| 25 | 100 | 0 | 20 | 0 |
| 26 | 100 | 15 | 47 | 0 |
| 27 | 100 | 100 | 100 | 100 |
| 31 | 100 | 100 | 100 | 100* |
| 32 | 100 | 100 | 100 | 100* |
| 33 | 100 | 100 | 95 | 100 |
| 34 | 100 | 100 | 100 | 100 |
| 35 | 100 | 100 | 95 | 100 |
| 36 | 100** | 97.5** | 97.5** | 100** |
| 43 | 100 | 100 | 95 | 100 |
| 44 | 100 | 100 | 100 | 100 |
| 49 | 100 | 100 | 100 | 100 |
| 50 | 100 | 100 | 100 | 100 |
| 53 | 100** | 100** | 94** | 100** |
| 54 | 100 | 95 | 100 | 100 |
| 57 | 100 | 75 | 55 | 90 |
| 60 | 100 | 100 | 100 | 100 |
| 66 | 100 | 90 | 100 | 100 |
| 72 | 100 | 100 | 100 | 100 |
| 75 | 100 | 100 | 100 | 100 |
| 78 | 100 | 40 | 75 | 26 |
| 79 | 100 | 65 | 100 | 60 |
| 95 | 100 | 85 | 100 | 100 |
| 96 | 100 | 95 | 100 | 100 |
| 98 | 30 | 100 | 100 | 100 |
| 99 | 30 | 100 | 100 | 100 |
| 102 | 100 | 98* | 100* | 100* |

[1] the total number of moribund insects (TM) as compared to the total number of insects (TI) used in the test:

$$\% \text{ Control} = \frac{TD + TM}{TI} \times 100$$

[2] TBW is tobacco budworm (*Heliothis veriscens* [Fabricius])
[3] CL is cabbage looper (*Trichoplusia ni* [Hubner])
[4] BAW is beet armyworm (*Spodoptera exigua* [Hubner])
*Rate of application is 30 ppm
** Average of more than one test

What is claimed is:

1. A compound of the formula:

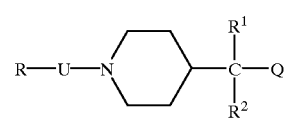

wherein U is —$(CH_2)_n$—; Q is hydroxy and R is represented by the following formula:

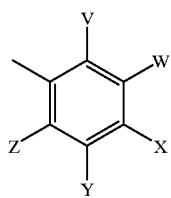

and wherein:

V, W, Y, and Z are each hydrogen;

X is a five- or six-membered heterocycle, optionally substituted with bromine, chlorine, fluorine, alkyl, alkoxyl, alkoxyalkyl, cyano, aminocarbonyl, haloalkyl, haloalkoxyl, or haloalkoxyalkyl; and the heterocycle is optionally connected to the phenyl ring through a —O—, —S—, —(CH$_2$)$_p$—, —C(O)—, or —O(CR$^3$R$^4$)$_q$— linkage;

R$^1$ and R$^2$ are independently selected from: (i) phenyl or pyridyl substituted with pentahalothio, haloalkylthio, haloalkylsulfinyl, or haloalkylsulfonyl; (ii) phenyl substituted with —OC(M)$_2$O—, where M is bromine, chlorine or fluorine, to provide a dihalobenzodioxolyl fused ring; or (iii) pyridyl substituted with —OC(M)$_2$O— to provide a dihalodioxolenopyridyl fused ring;

R$^3$ and R$^4$ are independently selected from hydrogen and methyl;

n and p are independently 1, 2, or 3, and q is 1 or 2;

with the proviso that at least one of said R$^1$ and R$^2$ is substituted in the para position of the phenyl ring or the 5-position of the 2-pyridyl ring; each alkyl portion of said optional substituent on X wherein the optional substituent is alkyl, haloalkyl, alkoxyl, haloalkoxyl, alkoxyalkyl, or haloalkoxyalkyl contains from 1 to 4 carbon atoms; each said heterocycle representing X contains from 1 to 4 nitrogen atoms, 1 or 2 oxygen or sulfur atoms, or 1 or 2 nitrogen atoms and an oxygen or sulfur atom, and corresponding N-oxides and agriculturally acceptable salts thereof.

2. The compound of claim 1 wherein the heterocycle representing X is selected from the group consisting of 1,2,4-oxadiazol-5-yl, oxazolin-2-yl, pyrazol-3-yl, pyridin-2-yl, pyrimidin-2-yl, pyrol-3-yl, 2H-tetrazol-5-yl, 1,2,3-thiadiazol-4-yl, and 1,2,4-triazol-3-yl, optionally substituted with halogen, alkyl, alkoxyl, alkoxyalkyl, cyano, aminocarbonyl, or haloalkyl, and the optional linkage is selected from —O—, —(CH$_2$)$_p$—, —C(O)—, or —O(CHR$^3$)$_q$—.

3. The compound of claim 1, wherein said R$^1$ and R$^2$ are independently selected from the group consisting of pentafluorothiophenyl, trifluoromethylthiophenyl, trifluoromethylsulfinylphenyl, trifluoromethylsulfonylphenyl, 2,2dihalo-1,3-benzodioxolyl, pentafluorothiopyridyl, trifluoromethylthiopyridyl, trifluoromethylsulfinylpyridyl, trifluoromethylsulfonylpyridyl, and 2,2-dihalo-1,3-dioxoleno[4,5-b]pyridyl.

4. The compound of claim 1, wherein the heterocycle representing X is selected from the group consisting of 1,2,4-oxadiazol-5-yl, oxazolin-2-yl, pyrazol-3-yl, pyridin-2-yl, pyrimidin-2-yl, pyrol-3-yl, 2H-tetrazol-5-yl, 1,2,3-thiadiazol-4-yl, and 1,2,4-triazol-3-yl, optionally substituted with chlorine, fluorine, alkyl, alkoxyl, alkoxyalkyl, cyano, aminocarbonyl, or haloalkyl, and the optional linkage is selected from —O—, —(CH$_2$)$_p$—, —C(O)—, or —O(CHR$^3$)$_q$—; said R$^1$ and R$^2$ are independently selected from the group consisting of pentafluorothiophenyl, trifluoromethylthiophenyl, trifluoromethylsulfinylphenyl, trifluoromethylsulfonylphenyl, 2,2-dihalo-1,3-benzodioxolyl, pentafluorothiopyridyl, trifluoromethylthiopyridyl, trifluoromethylsulfinylpyridyl, trifluoromethylsulfonylpyridyl, and 2,2-dihalo-1,3-dioxoleno[4,5-b]pyridyl; n is 1 and p and q are independently selected from 1 and 2; and M is chlorine or fluorine.

5. The compound of claim 1 wherein the heterocycle representing X is selected from the group consisting of 1,2,4-oxadiazolyl, oxazolinyl, pyridazinyl, pyrazinyl, pyrazolyl, pyridyl, pyrimidinyl, pyrolyl, tetrazolyl, 1,2,3-thiadiazolyl, 1,3,5-triazinyl, and 1,2,4-triazolyl.

6. The compound of claim 1 wherein when q is 2, —O(CR$^3$R$^4$)$_q$— is selected from the group consisting of —O(CHCH$_3$CHCH$_3$)—, —O(C(CH$_3$)$_2$CH$_2$)— and —O(CH$_2$C(CH$_3$)$_2$)—.

7. The compound of claim 2 wherein the optional substituent on X is selected from the group consisting of alkyl, alkoxyl, cyano, haloalkyl and CH$_2$OCH$_3$, wherein said haloalkyl is —(CH$_2$)$_r$F, where r is 1, 2, or 3, CHF$_2$, CF$_3$; the optional linkage is selected from the group consisting of —O—, —OCH$_2$—, and —OCH(CH$_3$); and both R$^1$ and R$^2$ are independently selected from the group consisting of p-pentafluorothiophenyl and 2,2-difluoro-1,3-benzodioxol-5-yl.

8. The compound of claim 2 wherein the heterocycle representing X is 2H-tetrazol-5-yl substituted in the 2-position.

9. The compound of claim 8 selected from the group consisting of N-[4-(2-methyl-2H-tetrazol-5yl)phenylmethyl]-4-[bis(4-pentafluorothiophenyl)hydroxymethyl]piperidine, N-[4-(2-methyl-2H-tetrazol-5-yl)phenylmethyl]-4-[bis(4-pentafluorothiophenyl)hydroxymethyl]piperidine N-oxide, N-[4-(2-ethyl-2H-tetrazol-5yl)phenylmethyl]-4-[bis(2,2-difluoro-1,3-benzodioxol-5-yl)hydroxymethyl]piperidine, N-[4-(2-ethyl-2H-tetrazol-5-yl)phenylmethyl]-4-[bis(2,2-difluoro-1,3-benzodioxol-5-yl)hydroxymethyl]piperidine N-oxide, and N-[4-[2-(2-fluoroethyl)-2H-tetrazol-5-yl]phenylmethyl]-4-[bis(2,2-difluoro-1,3-benzodioxol-5-yl)hydroxymethyl]piperidine.

10. The compound of claim 2 wherein the heterocycle representing X is pyridin-2-yl substituted in the 6-position.

11. The compound of claim 10 is selected from the group consisting of N-[4-(pyridin-2-yl)phenylmethyl]-4-[bis(2,2-difluoro-1,3-benzodioxol-5-yl)hydroxymethyl]-piperidine and N-[4-(pyridin-2-yloxy)phenylmethyl]-4-[bis(2,2-difluoro-1,3-benzodioxol-5-yl)hydroxymethyl]piperidine.

12. The compound of claim 2 wherein the heterocycle representing X is pyrimidin-2-yl substituted in the 4-position.

13. The compound of claim 12 is selected from the group consisting of N-[4-(pyrimidin-2-yloxy)phenyl-methyl]-4-[bis(2,2-difluoro-1,3-benzodioxol- 5-yl)hydroxymethyl]piperidine and N-[4-(pyrimidin-2-yl)phenylmethyl]-4-[bis(2,2-difluoro-1,3-benzodioxol-5-yl)hydroxymethyl]piperidine.

14. The compound of claim 3 wherein R$^1$ and R$^2$ are independently selected from the group consisting of 5-pentafluorothiopyrid-2-yl and 2,2-difluoro-1,3dioxoleno[4,5-b]pyrid-5-yl.

15. The compound of claim 14 is N-[4-(2-ethyl-2H-tetrazol-5-yl)phenylmethyl]-4-[bis(2,2-difluoro-1,3-dioxoleno[4,5-b]pyrid-5-yl)hydroxymethyl]piperidine.

16. An insecticidal composition comprising an insecticidally effective amount of a compound of claim 1 in admixture with at least one agriculturally acceptable carrier.

17. A method of controlling insects comprising the step of applying to a locus where control is desired an insecticidally effective amount of a composition of claim 15.

* * * * *